(12) United States Patent
Zoughi et al.

(10) Patent No.: US 6,614,240 B2
(45) Date of Patent: Sep. 2, 2003

(54) MICROWAVE DETERMINATION RELATED TO A MATERIAL SUCH AS CHLORIDE FOUND IN A CEMENT BASED COMPOSITION

(75) Inventors: Reza Zoughi, Wildwood, MO (US); Aaron D. Benally, Fort Collins, CO (US); Karl J. Bois, Fort Collins, CO (US); Kimberly Kurtis, Atlanta, GA (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 09/907,400

(22) Filed: Jul. 16, 2001

(65) Prior Publication Data
US 2002/0057095 A1 May 16, 2002

Related U.S. Application Data
(60) Provisional application No. 60/219,461, filed on Jul. 18, 2000.

(51) Int. Cl.⁷ .............................................. G01R 27/04
(52) U.S. Cl. ...................... 324/646; 324/632; 324/643; 324/647
(58) Field of Search .................. 324/637, 639, 324/640, 643, 646; 73/290 R, 290 V

(56) References Cited
U.S. PATENT DOCUMENTS 3,562,642 A * 2/1971 Hochschild ................. 324/642
4,832,803 A * 5/1989 Vennesland et al. ......... 427/540
5,939,889 A    8/1999 Zoughi et al. .............. 324/643

OTHER PUBLICATIONS

W. Shalaby and R. Zoughi, "Microwave Compressive Strength Estimation of Cement Paste Using Monopole Probes", Res Nondestr Eval (1955) 7:101–115, Springer–Verlag New York Inc. No month available.

* cited by examiner

Primary Examiner—N. Le
Assistant Examiner—Vincent Q. Nguyen
(74) Attorney, Agent, or Firm—Sheridan Ross. P.C.

(57) ABSTRACT

Determinations are made related to the presence of a predetermined material in concrete under test using previously obtained model information. In one embodiment, the predetermined material includes a chloride material and the model information is obtained using a number of cured cement specimens. The model information is stored in memory, such as in the form of a look-up table. When the concrete is being inspected, one or more magnitudes of reflections coefficients are measured and such is utilized with the model information to make determinations related to the presence of the predetermined material. In developing the model information, each of the plurality of cured cement specimens is located in a bath containing the predetermined material. The bath may be pressurized. The cured cement specimens are maintained in the bath for different, known time intervals. After the known time interval for a particular specimen, it is dried and one or more magnitudes of reflection coefficients are measured. This data is utilized in preparing the model information.

5 Claims, 19 Drawing Sheets

Magnitude of reflection coefficient over time for cement mortar specimens at S-band (3 GHz)

Magnitude of reflection coefficient over time for cement mortar specimens at X-band (10 GHz)

Magnitude of reflection coefficient over time for cement mortar specimens at S-band (3 GHz)

Curve fit of magnitude of reflection coefficient over time for cement mortar specimens at S-band (3 GHz)

Magnitude of reflection coefficient over time for cement mortar specimens at X-band (10 GHz)

Curve fit of magnitude of reflection coefficient over time for cement mortar specimens at X-band (10 GHz)

Magnitude of all reflection coefficients over time for cement mortar specimens at S-band (3 GHz)

Curve fit of magnitude of all reflection coefficient over time for cement mortar specimens at S-band (3 GHz)

Magnitude of all reflection coefficients over time for cement mortar specimens at S-band (3 GHz)

Curve fit for magnitude of all reflection coefficients over time for cement mortar specimens at S-band (3 GHz)

The plot of the compressive strength measured after the curing period for w/c=0.50

The plot of the compressive strength measured after the curing period for w/c=0.60

Strength curves due to NaCl with w/c=0.50

Strength curves due to NaCl with w/c=0.60

Linear plot of $|\Gamma|$ at day 28 vs. NaCl/c for w/c=0.50

Linear plot of $|\Gamma|$ at day 28 vs. NaCl/c for w/c=0.60

Linear plot of strength vs. $|\Gamma|$ at day 28 for w/c=0.50

Linear plot of strength vs. $|\Gamma|$ at day 28 for w/c=0.60

Relative permittivity of water vs. frequency at 20°C for varying salinity

Loss factor of water vs. frequency at 20°C for varying salinity

Coring

MICROWAVE DETERMINATION RELATED TO A MATERIAL SUCH AS CHLORIDE FOUND IN A CEMENT BASED COMPOSITION

The present application relates to and claims priority from prior U.S. Provisional Patent Application No. 60/219,461 filed Jul. 18, 2000, which is incorporated herein by reference.

The invention described herein was made in the performance of work under a National Science Foundation grant identified by #CMS-9817695.

FIELD OF THE INVENTION

This relates to the determination of the content of one or more materials in a cement containing composition, such as the amount of chloride in a cement based composition.

BACKGROUND OF THE INVENTION

The construction industry is interested in new techniques for nondestructive inspection of materials. Currently the techniques used are adequate in some cases, but may not be the case in others. One solution to this problem would be to combine one technique with others.

Chloride has been found to corrode steel members in reinforced structures. In solving this problem, early detection and close monitoring of chloride contaminated structures is essential in maintaining these structures. A nondestructive technique for determining chloride contamination would be beneficial.

Research has found that non-conducting materials, i.e. dielectric materials, can be analyzed by using microwave nondestructive testing (NDT) techniques. Microwave NDT techniques have been used to find surface and sub-surface degeneration in layered materials due to impact damage, and to measure the thickness of dielectric sheets. Such techniques also find unfilled spaces and air bubbles (locally and distributed) in dielectric materials, and are used to locate and evaluate disbond and delamination in multi-layered structures. Microwave signals can be used to measure the dielectric properties of a material. By knowing the dielectric properties of cement, aggregate, and sand, microwave signals can be used to measure the properties of the combined mixture. Also, this can be used to determine the curing rate and the presence of chemical reactions in the mixture.

Research has been conducted in this area. It has been found within recent years that this technique can be utilized for inspecting cement based construction composition. Near and far field techniques were the two main groups studied. The near and far field regions are based on the distance in which the sensor and the composition are separated from each other. Ground penetrating radars are an example of a far field technique and have been used successfully. Although it has been a success, there are still disadvantages to this technique. For example, repetitious calibration of the measurement equipment, the system spatial resolution, the inaccuracy of the data needed due to unwanted objects and the tedious signal processing needed to analyze the data are drawbacks. These are avoided when using the near field technique. The setback of operating in this region is that the electric and magnetic fields are very complicated to model.

The measured magnitude of reflection coefficient is shown to increase as a function of decreasing w/c ratio for cured cement paste. At first glance this seems inconsistent with the fact that higher water content should render a higher magnitude of reflection coefficient measured at a waveguide aperture. However, a closer look reveals that during the curing process water molecules bond with cement molecules, and some of the remaining free water evaporates. Thus, the water becomes less free and more bound over the curing time. Free water has much higher dielectric properties compared to those of cement powder, whereas bound water has similar dielectric properties to those of cement powder. In addition, higher w/c ratio specimens lose more of their free water to evaporation. Thus, the measured magnitude of reflection coefficient of these specimens decreases as a function of increasing w/c ratio.

The magnitude of reflection coefficient has been shown to be distinctly correlated to the w/c ratio of cement paste, and subsequently to its 28-day compressive strength (moist cured for 3 days in a hydration and thereafter in an air room temperature).

A simple expression predicting the microwave reflection properties of cement paste as a function of time has been obtained. Consequently, the w/c ratio of a cement paste specimen may be obtained by comparing two reflection coefficient measurements conducted several hours or a few days apart after the paste has been cast. In addition, it is possible to correlate the compressive strength of cement paste during curing to the measured microwave reflection properties (as a percentage of the 28-day strength).

A relationship between the standard deviation of the magnitude of reflection coefficient at higher frequencies and the s/c (sand/cement) ratio of a mortar specimen, has been established. Information on the w/c ratio of mortar specimens is obtained when the average value of the measurements is taken at relatively low microwave frequencies.

Mortar is a homogeneous dielectric mixture (even when measured at a frequency of 10 GHz). A simple dielectric mixing model has been obtained which predicts the constituent volume content of a mortar specimen. Consequently, the porosity (volume content of distributed air) of a mortar specimen can also be determined.

The statistical behavior of the microwave reflection properties of concrete as a function of w/c, s/c and ca/c (coarse aggregate/cement) ratios and the frequency of operation has been studied. It has been determined that the probability distribution functions of the measured magnitude of reflection coefficient of concrete, measured at high and low frequency bands, possess distinct and well-known distributions. At higher frequencies, the distribution is Gaussian whereas at low frequencies the distribution is uniform. With the use of the modifiable parameters in each of these distributions, the constituent volume distribution of a given concrete mixture can be determined from its scattering characteristics.

Similar to mortar, the results of the reflection property measurements indicate that the w/c ratio in concrete, and hence its strength, can be correlated to the average value of the magnitude of reflection coefficient measured at several independent locations on a specimen at lower frequencies (i.e., about 3 GHz). At lower frequencies the influence of aggregate size distribution is less on the measured magnitude of reflection coefficient than at higher frequencies since the aggregates electrically "look smaller" at lower frequencies.

Similarly, the standard deviation and the statistical distribution of the measured magnitude of reflection coefficient at higher frequencies is a function of the aggregate size and volume distributions. Hence, the constituent volume fraction and distribution of a concrete specimen may be determined at higher frequencies (i.e., about 10 GHz).

It has been shown that the cure state of concrete specimens, containing different w/c ratios and constitute makeup, can be unambiguously determined when making daily measurements of the magnitude of reflection coefficient.

It has also been shown that the w/c ratio of fresh concrete can be unambiguously determined independent of its s/c and ca/c ratios. This is an important finding since now an operator is capable of determining the w/c ratio of a batch plant concrete at the time of pouring.

It has been demonstrated that the extent of aggregate segregation in concrete placement can be evaluated using the statistics of the measured magnitude of reflection coefficient. This information can be easily obtained for concrete members such as walls and columns in which aggregate segregation may be an important practical issue.

Using an optimal frequency of operation, it has been effectively demonstrated that using a simple near-field and nondestructive microwave inspection technique employing an open-ended rectangular waveguide probe at 3 GHz (S-band) one can easily distinguish between empty and grout-filled masonry cells. In addition, a simple and extremely effective custom-built microwave inspection system has been designed and assembled for this purpose. This system has been successfully tested on a variety of masonry blocks.

Up to this point, the near field microwave NDT technique has been successfully applied to the inspection and characterization of cement based materials in several studies including detection of rebar in reinforced concrete; determination of variations in aggregate size distribution in concrete; determination of compressive strength and water-to-cement (w/c) ratio of hardened cement paste (cement and water); prediction of the microwave reflection properties of mortar (cement, sand and water) using a dielectric mixing model as a tool for obtaining the volume fraction of individual constituents of mortar; determination of the distributed porosity in mortar; determination of sand-to-cement ratios in mortar using the stochastic properties of its microwave reflection properties; and determination of the coarse aggregate volumetric distribution in concrete.

Concrete normally provides reinforcing steel with adequate corrosion protection. When steel is encased in concrete, a protective iron oxide film forms at the steel-concrete interface due to the high pH level associated with concrete. This film protects the steel from corrosion. However, the intrusion of chloride ions in reinforced concrete can destroy this protective film. If moisture and oxygen are present in the concrete, the steel will corrode through an electrochemical process. Once the steel begins to corrode, the concrete will deteriorate. This occurs because the byproducts of corrosion occupy a greater volume than the steel itself, which exerts a substantial stress on the surrounding concrete.

SUMMARY OF THE INVENTION

In accordance with the present invention, a determination is made related to the presence of at least one predetermined material in concrete or cement sample. In one embodiment, the material is one that is not normally included when the concrete is formed. For example, the material can be a salt that may include chloride. The salt may penetrate the concrete after it is formed. Alternatively or additionally, at least parts of the salt might have been included with the concrete when it was made. In one embodiment, the presence of the predetermined material is detected. Additionally or alternatively, the amount of the predetermined material is determined. Additionally or alternatively, a magnitude is determined related to the penetration of the predetermined material in the concrete, particularly the depth that the material might be found from the surface of the concrete.

An apparatus that can be used to make one or more such determinations includes a signal generating subsystem, a coupler subsystem and an analyzer subsystem. With regard to making one or more such determinations, the signal generating subsystem outputs microwave signals that are applied to the coupler subsystem. The coupler subsystem includes a transmitting section that carries the microwave signals to the concrete that is under observation or test. Reflected or returned microwave signals are generated due to the incidence of the transmitted microwave signals on the concrete sample. These are received by the receiving section of the coupler subsystem. These returned microwave signals are input to the analyzer subsystem, which makes the determinations related to the presence, amount and/or penetration associated with the predetermined material.

The analyzer subsystem includes at least one memory. The memory stores model information related to the predetermined material. In particular, the model information includes data or other information related to the predetermined material and one or more magnitudes of reflection coefficients. These are obtainable from the reflected microwave signals. They are useful in making the determinations related to the predetermined material. The model information is obtained based on measurements made using cement samples that were previously analyzed under known conditions. The model information that is obtained based on such testing and measurements can be presented in many different or related forms, such as an equation, a graph and/or a look-up table. The model information correlates the predetermined material in the concrete and associated dielectric property information (e.g., reflection coefficient magnitudes). Thus, when making determinations related to the predetermined material for the concrete under test or in the particular cement sample, the one or more reflection coefficient magnitudes measured using the cement sample are found and these determined magnitudes are used to make determinations related to the predetermined material, such as by use of a look-up table that correlates the determined one or more reflections coefficient magnitudes with formation related to the predetermined material of interest.

With respect to obtaining the data or other information to which the reflection coefficient magnitudes are to be correlated, certain steps are conducted associated with making measurements to provide such information. More specifically, a cured cement specimen is made or otherwise provided. The cured cement specimen may include some predetermined material or it may not. The cured cement specimen is located in a bath associated with known conditions. In one embodiment, the bath is a salt bath that has chloride as the predetermined material. The cured cement specimen is maintained in the salt bath for a desired or known time interval. The cement specimen is removed from the bath after the known time interval. It is allowed to dry. Then, one or more magnitudes of reflection coefficients are measured for this cement specimen. Later at different time intervals, one or more additional magnitudes of reflection coefficients are determined. This is continued until there is essentially no change in the measured magnitudes of reflection coefficients or such measurements are within an acceptable variation of each other.

Additional cured cement specimens are provided. For each of the cement specimens, the foregoing steps are implemented. For at least some of these cement specimens, they are placed in the bath having the predetermined material for different, known time intervals. Accordingly, measurements of magnitudes of reflection coefficients for other cement specimens are made after different time intervals related to how long the particular cement specimen remained in the bath.

In conjunction with obtaining model information related to the predetermined material in a particular cement sample, it may be desirable to further analyze the cement specimens after the one or more measurements of the magnitudes of reflection coefficients. In such a case, a cement specimen may have one or more sections removed therefrom. In one embodiment, a cylindrical cored section is removed from which a number of smaller in height cylindrical sections (slices) are severed. Subsequently, the cored portions are ground. The ground portions are subject to an analysis step involving an instrument, such as an electron microscope or the x-ray fluorescent machine, which can provide information related to the content of the predetermined material in the cement specimen. Such analysis can verify the accuracy of the measuring step, as well as provide information related to penetration of the predetermined material within the body of the concrete specimen from its surface.

Based on the foregoing summary, a number of advantages of the present are readily discerned. Information related to the presence, amount and/or penetration of a predetermined material in concrete can be obtained using model information. The model information can include chloride model information. The present invention is useful when the predetermined material is included with and/or becomes part of the concrete after it has been formed. Substantial and extensive testing is conducted to obtain the model information, particularly using a number of cement samples that have been cured and are subject to a bath having the predetermined material. Utilizing model information, such as chloride model information, the salt or chloride content of concrete can be monitored over time related to ascertaining currently existing properties of the concrete, such as whether its structural integrity is jeopardized by unacceptable levels of salt content.

Additional advantages of the present invention will become readily apparent from the following discussion, particularly when taken together with the accompanying drawings.

DETAILED DESCRIPTION

Figure 1:
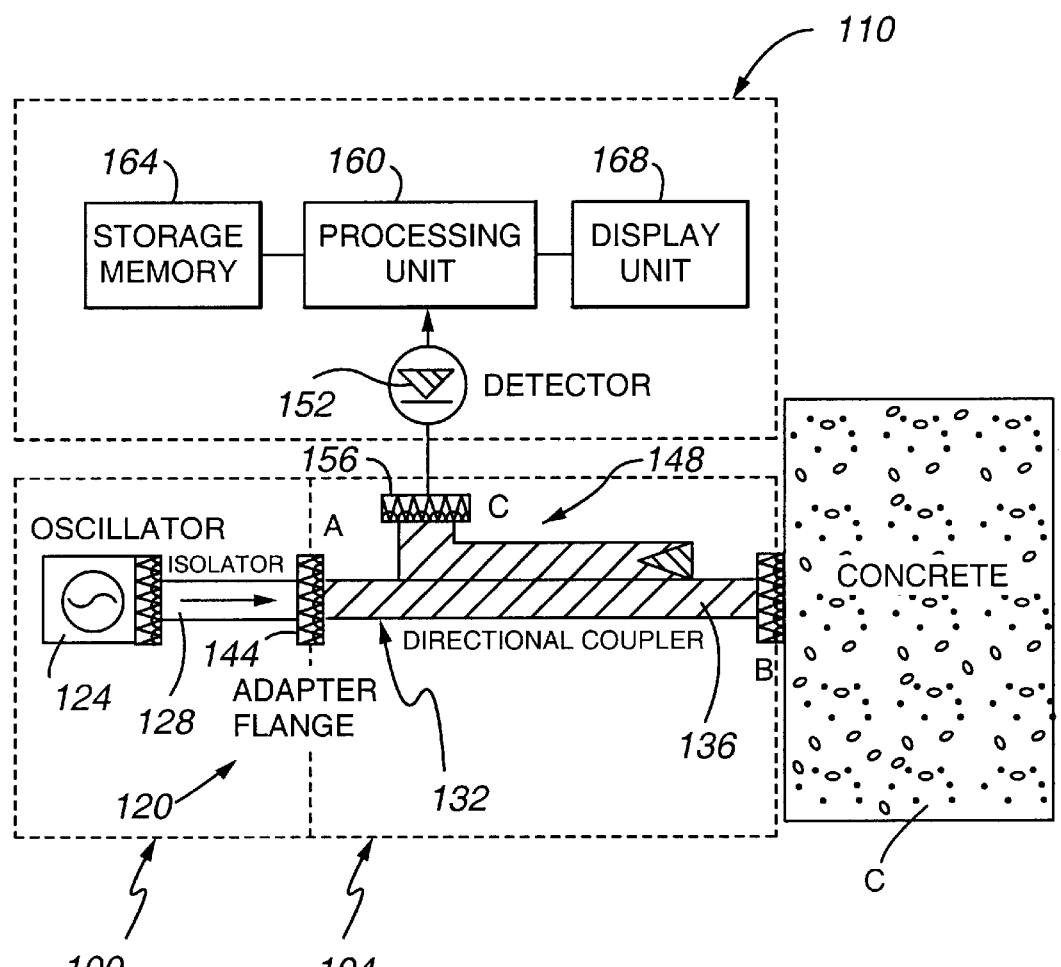
FIG. 1 is a block diagram of the apparatus of the present invention.

With reference to FIG. 1, one embodiment of an apparatus is illustrated for making determinations and obtaining information related to a predetermined material in concrete C under test. This embodiment includes a signal generating subsystem 100 that outputs microwave signals at desired frequencies and which are to come in contact with the concrete under test. The signal generating subsystem 100 communicates with a coupler subsystem 104. The coupler subsystem 104 receives the microwave signals from the signal generating subsystem 100 and controllably directs them to the concrete. Return or reflected signals are returned from the concrete under test to the coupler subsystem 104 and are applied to an analyzing subsystem 110. The analyzing subsystem 110 is involved with making determinations related to the presence, amount, and/or penetration of the predetermined material that may be found in the concrete. In one embodiment, the predetermined material is a salt, such as a chloride material.

The coupler subsystem 104 includes an oscillator 124 for generating microwave signals at any one of a number of selected and desired microwave frequencies. The output of the oscillator 124 is input to an isolator 128 that receives the inputted microwave signals and isolates the signals from any unwanted signals entering the oscillator 124. The coupler subsystem 104 has a microwave transmitting section 136 and a microwave receiving section 140. The transmitting section 136 is connected to the isolator 128 by means of a first adaptor or flange 144. The transmitting section 136 is preferably in contact with, but may be spaced from, the concrete sample C. The transmitting section 136 directs the transmitted microwave signals relative to the concrete sample. The transmitted microwave signals are incident upon the concrete sample, with some of the microwave energy being absorbed. Reflected microwave signals are generated due to the incidence of the transmitted microwave signals upon the concrete sample and the reflected microwave signals are received by the receiving section 140 of the coupler subsystem 104. The receiving section 140 is part of a receiver assembly 148 that receives the reflected microwave signals in order to measure the signals in connection with the determining a reflection coefficient magnitude (Γ) associated with the concrete sample. That is, a reflection coefficient magnitude (Γ) is determined with reference to the reflection plane defined at the concrete sample edge that is contacted by the transmitting section 136. In making the measurement, the receiving section 140 of the coupler subsystem 104 communicates with a crystal detector 152 of the receiver assembly 148. The receiving section 140 is connected to the crystal detector 152 by means of a second adaptor or flange 156. The crystal detector 152 generates a signal as a function of the reflected and received microwave signals. The signal is applied to a processing unit 160 of the analyzing subsystem 110 for use in automatically analyzing the reflected microwave signals in order to determine information related to the predetermined material such as values related to chloride in the sample of concrete C. This will be discussed in more detail later herein. The processing unit 160 communicates with storage memory 164 for storing program code (software), together with information or data useful in correlating or otherwise using previously determined model information with the measured reflected microwave signals. As can be appreciated, the storage memory 164 can be one or more discrete memory devices or components. A display unit 168 can also be provided so that the user can immediately see information related to the analysis that is conducted relative to the predetermined material that might be in the concrete sample C.

Substantial portions of the following description will be in the context of the predetermined material including a chloride material, although it should be appreciated that other predetermined materials, as it relates to determining their presence, amount and/or penetration in concrete can be utilized with the present invention.

Figure 2:
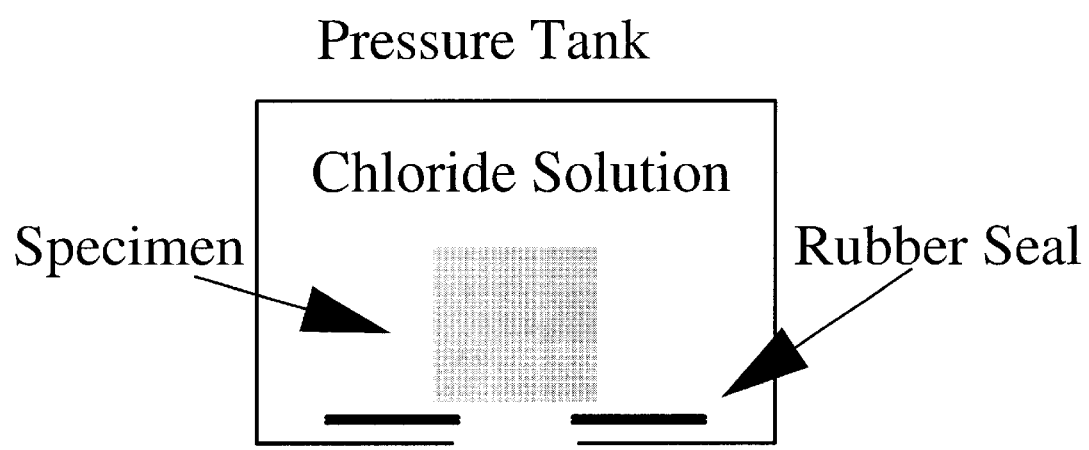
FIG. 2 diagrammatically illustrates a cured concrete specimen located in a pressure tank that includes, in one embodiment, a chloride solution.

In order to detect and evaluate chloride penetration in cement based materials (in particular concrete) one must have access to specimens in which chloride ions have penetrated (including successive penetration simulating real-life exposure of concrete to chloride). Furthermore, these specimens must contain various amounts of chloride so that minimum chloride content detection can be established for this particular near-field microwave technique. Consequently, the following procedure is followed:

Referring to FIG. 2, subject the specimens mentioned above (after they have been cured for 28 days and their microwave reflection properties have been measured daily) to a chloride solution in an enclosed tank under pressure and controlled temperature. The chloride content in the solution, the pressure level and the amount of time required will be varied. The pressure level and the length of time during which the pressure is applied will primarily influence the depth to which the chloride penetrates into the specimens, while the chloride content affects the amount of present chloride. This provides a wide range of results (i.e. the amount of chloride present in the samples and the depth to which they have penetrated). This procedure is conducted several successive times. At each iteration, the microwave reflection properties of the specimens are measured, to replicate chloride penetration over several successive contaminations. To ensure that the chloride solution replaces the air voids in the specimens, a section of the tank bottom is removed and the specimen will be placed (using a rubber seal) in such a way that the air voids can escape from it when the pressure is applied, as shown below. The amount of air that will escape is a function of the w/c ratio, s/c ratio and ca/c ratio of the specimens.

It is imperative that the overall content of chloride that has been added to a specimen be known each time the specimen is subjected to the chloride solution. Therefore, the specimens are weighed, using a sensitive scale, before and after being subjected to the chloride solution under pressure. Furthermore, the specimens will be weighed every day, throughout the period during which their microwave reflection properties are being measured (after removal from the tank). In this way the amount of water that evaporates during the first few days, after the specimens have been removed from the chloride solution, will be known as well. The information regarding the amount of chloride in the specimen, the amount of water and its subsequent evaporated amount, will be incorporated in the analysis of the overall results when the microwave reflection properties are being analyzed. The soaking period should not permit re-hydration.

Chlorides can be introduced into concrete in many ways. They may be introduced into the concrete mix by the aggregates, cement, admixtures and/or the mixing water. Moreover, chlorides may enter into a concrete structure, while in use, through exposure to deicing salts, seawater or salt air environment. Since chlorides can be introduced through many mechanisms, placing limits on any one of concrete constituents (e.g. mixing water) may not always limit the total amount of chloride in the concrete. Therefore, it is important to be able to measure the chloride content of concrete in order to indicate the likelihood of corrosion of its embedded reinforcing steel bars.

The limit placed on the amount of chloride content in concrete is a function of the type of structure and the environment to which it is exposed during usage. Limits on chloride content in reinforced concrete are set in two ways: water-soluble chloride ion content, and the total chloride ion content. The two values are not substantially different from one another because the water-soluble chlorides are only a part of the total chloride content, namely, the free chloride in the water.

Steel in concrete begins to corrode when the water soluble chloride content in the concrete is about 0.15% of the cement weight. Of the total chloride ion content in concrete, only about 50% to 80% is water soluble, the rest becomes chemically bound in the chemical process involving cement. Limits on the water-soluble chloride content in concrete have been set by the American Concrete Institute. These limits, as a percentage (of the cement weight) are 0.06% for prestressed concrete, 0.15% for reinforced concrete exposed to chloride in service, 1.00% for reinforced concrete that remains dry or is protected from moisture in service, and 0.30% for other reinforced concrete structures. The water-soluble chloride ion content of hardened concrete may be determined by a procedure similar to that reported in a Federal Highway Administration (FHWA) Report by Clear and Harrigan. This procedure is destructive in nature and is performed in a laboratory on concrete that has hardened for 2 to 42 days.

The standard approaches for determining the level of chloride content in concrete (i.e. the total amount of chlorides) are the procedures outlined by the American Society for Testing and Materials (ASTM) and the American Association of State Highway and Transportation Officials (AASHTO). Both of these standards require that a core be extracted from the structure under inspection, which is ground into a powder, and subsequently tested in a laboratory to obtain its chloride content. Limits on the total chloride content in reinforced concrete have been set at 0.40% of the cement weight.

All of the methods mentioned for determining chloride content in concrete require obtaining a sample of the hardened concrete. Subsequently, it is ground up and tested following the procedures outlined in references. These methods present several distinct disadvantage such as being destructive, time consuming and prohibitive to the large scale testing of large structures. Moreover, these structures cannot be tested again at the same location for determining the progression of chloride penetration. Consequently, nondestructive solutions are highly advantageous for chloride detection.

As mentioned earlier, microwave NDT techniques have already demonstrated the ability to determine the w/c ratio in cement paste and mortar specimens. The success in doing this is mainly due to the inherent sensitivity of microwaves to the presence of bound or free water in these materials. In the case where the chloride content in a specimen is above a certain limit, the chloride will interact with any free (or bound) water and significantly affect its dielectric properties. It has already been shown that for a given microwave frequency range, an increase in the salinity of water significantly increases its microwave absorption characteristics. Based on this simple but sound principle, the detection and evaluation of chloride content in cement paste and mortar is quite feasible.

A near-field microwave nondestructive evaluation technique for detection and evaluation of chloride content in cement paste and mortar specimens is provided. This method uses the magnitude of reflection coefficient measurements measured at the aperture of an open-ended rectangular waveguide probe in S-band (2.6 GMz-3.95 GHz) and X-band (8.2 GHz-124 GHz).

The process of determining the content and curing effects of chloride on cement based compositions starts by making a set of 8" by 8" by 8" cement mortar cubic specimens. The first sets of mortar specimens were made with a water-to-cement ratio (w/c) of 0.50 and a sand-to-cement ratio (s/c) of 1.5. The second sets of mortar specimens were made with a w/c of 0.60 and a s/c of 1.5. Each specimen produced had a different amount of salt added to the water. Sets of seven samples were made for the w/c ratio of 0.50, Table 1 and 2 show the mixtures of the samples, and Table 3 and 4 shows the mixtures of the five samples made for w/c ratio of 0.60. Due to the number of specimens needed and only four cubic forms provided, two sets of data were obtained for each case. Along with making the cubic forms, four 4"×8" cylinders (of each salinity) were also made.

In Table 1, specimens 1–4 provided the first sets of data and specimens 5–7 provided the second set. In Table 3, specimens 3–5 provided the first set of data and specimens 1–2 provided the second set. Tables 2 and 4 set out weight amounts for the specimens of Tables 1 and 3, respectively. Each of these samples were moist cured in a hydration room for one day and air cured for the remaining 28 days. Every day the reflection properties of the specimens were monitored at S- and X-band using an apparatus of FIG. 1, which preferably included a HP8510 vector network analyzer. Twenty points were drawn on the sides of the blocks and measured at these same locations every day. After the 28 days of curing, the cylinders were tested for strength value with a compression machine. The data collected from both the network analyzer and compression machine were analyzed and such is found in Tables 5–7.

TABLE 1

Ratio of the individual constituents for the mortar specimens.

| Specimen | w/c ratio (by weight) | s/c ratio (by volume) | NaCl/c (%) (by weight) |
|---|---|---|---|
| 1 | 0.50 | 1.5 | 0.00 |
| 2 | 0.50 | 1.5 | 0.1 |
| 3 | 0.50 | 1.5 | 0.2 |
| 4 | 0.50 | 1.5 | 0.3 |
| 5 | 0.50 | 1.5 | 1.0 |
| 6 | 0.50 | 1.5 | 2.0 |
| 7 | 0.50 | 1.5 | 3.0 |

TABLE 2

Weight of the individual constituents for the mortar specimens.

| Specimen | Cement (lb.) | Water (lb.) | Sand (lb.) | Salt (lb.) |
|---|---|---|---|---|
| 1 | 25.256 | 12.628 | 31.751 | 0.000 |
| 2 | 25.256 | 12.628 | 31.751 | 0.025 |
| 3 | 25.256 | 12.628 | 31.751 | 0.051 |
| 4 | 25.256 | 12.628 | 31.751 | 0.076 |
| 5 | 25.256 | 12.628 | 31.751 | 0.253 |
| 6 | 25.256 | 12.628 | 31.751 | 0.505 |
| 7 | 25.256 | 12.628 | 31.751 | 0.760 |

TABLE 3

Ratio of the individual constituents for the mortar specimens.

| Specimen | w/c ratio (by weight) | s/c ratio (by volume) | NaCl/c (%) (by weight) |
|---|---|---|---|
| 1 | 0.60 | 1.5 | 0.00 |
| 2 | 0.60 | 1.5 | 0.5 |
| 3 | 0.60 | 1.5 | 1.0 |
| 4 | 0.60 | 1.5 | 2.0 |
| 5 | 0.60 | 1.5 | 3.0 |

TABLE 4

Weight of the individual constituents for the mortar specimens.

| Specimen | Cement (lb.) | Water (lb.) | Sand (lb.) | Salt (lb.) |
|---|---|---|---|---|
| 1 | 23.444 | 14.066 | 29.472 | 0.000 |
| 2 | 23.444 | 14.066 | 29.472 | 0.117 |
| 3 | 23.444 | 14.066 | 29.472 | 0.234 |
| 4 | 23.444 | 14.066 | 29.472 | 0.469 |
| 5 | 23.444 | 14.066 | 29.472 | 0.703 |

TABLE 5

Compressive strengths measured with the cylinders for w/c = 0.60.

| NaCl/c (%) | Height (in.) | Strength (psi) |
|---|---|---|
| 0.00 | 7⅝ | 4521.2 |
| 0.00 | 7½ | 4418.8 |
| 0.00 | 7⅝ | 5256.7 |
| 0.00 | 7¹¹⁄₁₆ | 4439.7 |
| 0.10 | 7⅝ | 5198.6 |
| 0.10 | 7¹¹⁄₁₆ | 5945.9 |
| 0.10 | 7¹³⁄₁₆ | 5235.9 |
| 0.10 | 7¾ | 5398.9 |
| 0.20 | 7⅝ | 6141.6 |
| 0.20 | 7¹¹⁄₁₆ | 5750.4 |
| 0.20 | 7¹³⁄₁₆ | 5810.9 |
| 0.20 | 7⅝ | 5918.0 |
| 0.30 | 7¹¹⁄₁₆ | 4579.4 |
| 0.30 | 7¹¹⁄₁₆ | 4328.0 |
| 0.30 | 7¹¹⁄₁₆ | 4486.3 |
| 0.30 | 7⅝ | 4553.8 |
| 1.0 | 7¾ | 5440.8 |
| 1.0 | 7¾ | 4889.0 |
| 1.0 | 7¾ | 5038.0 |
| 1.0 | 7⅞ | 4619.0 |
| 2.0 | 7¾ | 5557.1 |
| 2.0 | 7¾ | 4630.6 |
| 2.0 | 7⅝ | 5606.1 |
| 2.0 | 7¹¹⁄₁₆ | 5212.6 |
| 3.0 | 7¾ | 5913.4 |
| 3.0 | 7¹¹⁄₁₆ | 6064.7 |
| 3.0 | 7⁹⁄₁₆ | 6445.8 |
| 3.0 | 6¹⁵⁄₁₆ | 5665.0 |

TABLE 6

Compressive strengths measured with the cylinders for w/c = 0.60.

| NaCl/c | Strength (psi) | Average Strength |
|---|---|---|
| 0.00 | 2387.3 | 2407.2 |
| 0.00 | 2387.3 | |
| 0.00 | 2307.7 | |
| 0.00 | 2546.5 | |
| 0.50 | 4138.0 | 4085.5 |
| 0.50 | 4138.0 | |
| 0.50 | 3978.9 | |
| 0.50 | 3978.9 | |
| 1.0 | 3342.3 | 3302.5 |
| 1.0 | 3342.3 | |
| 1.0 | 3342.3 | |
| 1.0 | 3183.1 | |
| 2.0 | 3382.0 | 3561.1 |
| 2.0 | 3740.1 | |
| 2.0 | 3382.0 | |
| 2.0 | 3740.1 | |
| 3.0 | 4098.2 | 4118.1 |
| 3.0 | 4217.6 | |
| 3.0 | 4138.0 | |
| 3.0 | 4018.7 | |

TABLE 7

Conversion from NaCl/c percentage to actual Salinity percentage.

| NaCl/c (%) | 0.5 Salinity (%) | 0.6 Salinity (%) |
|---|---|---|
| 0.1 | 0.2 | N/A |
| 0.2 | 0.4 | N/A |
| 0.3 | 0.6 | N/A |
| 0.5 | N/A | 0.832 |
| 1.0 | 2.0 | 1.664 |
| Sea water | ~3.25 | ~3.25 |
| 2.0 | 4.0 | 3.334 |
| 3.0 | 6.0 | 4.998 |

Figure 11:
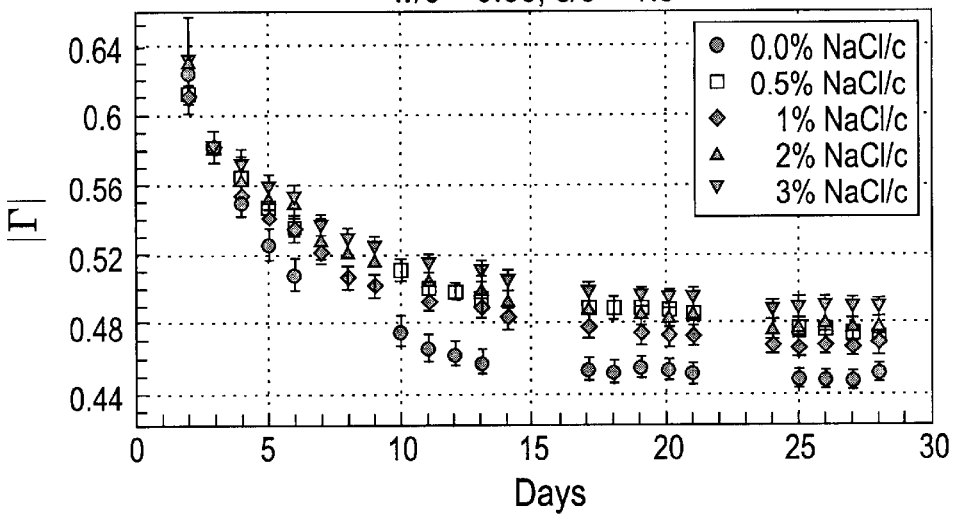
FIG. 11 is a graph illustrating magnitudes of all reflection coefficients for cement specimens measured at S-band for a different w/c ratio (0.60)
Figure 12:
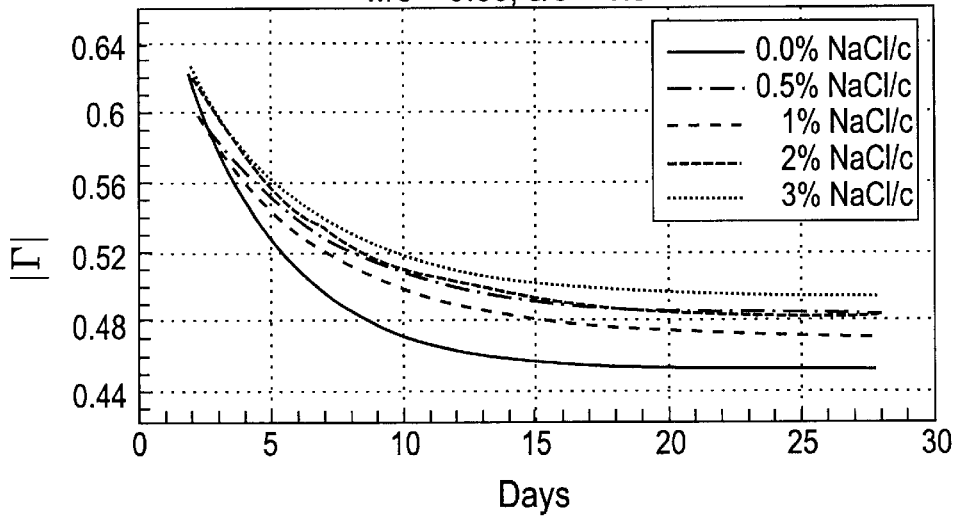
FIG. 12 is a graph illustrating curve fits for magnitudes of reflection coefficients for the cement specimens of FIG. 11.

FIGS. 3 through 10 show the results of 0.50 w/c ratio with varying NACl/c ratio. As expected, there is an exponential decrease in the magnitude of reflection coefficient, $|\Gamma|$, as a function of curing time. FIGS. 11 through 12 show the results of 0.60 w/c ratio with varying NaCl/c ratio. Again, a similar trend of $|\Gamma|$ as a function of time is observed. The exponential decrease is due in part to the evaporation of the free water molecules during the curing period and the chemical bonding of water to the cement molecules. Since microwave is highly sensitive to the presence of water, especially free water, the measurement of $|\Gamma|$ is expected to decrease as a function of curing time. Comparing both S-band plots (FIGS. 3 and 11) of 0.50 and 0.60 w/c ratios, the measurement of $|\Gamma|$ for the specimens with w/c=0.50 is consistently greater than those containing 0.60 w/c ratio. Additionally, per given w/c ratio, the data shows distinction between percentage of sodium chloride for each specimen.

Figure 3:
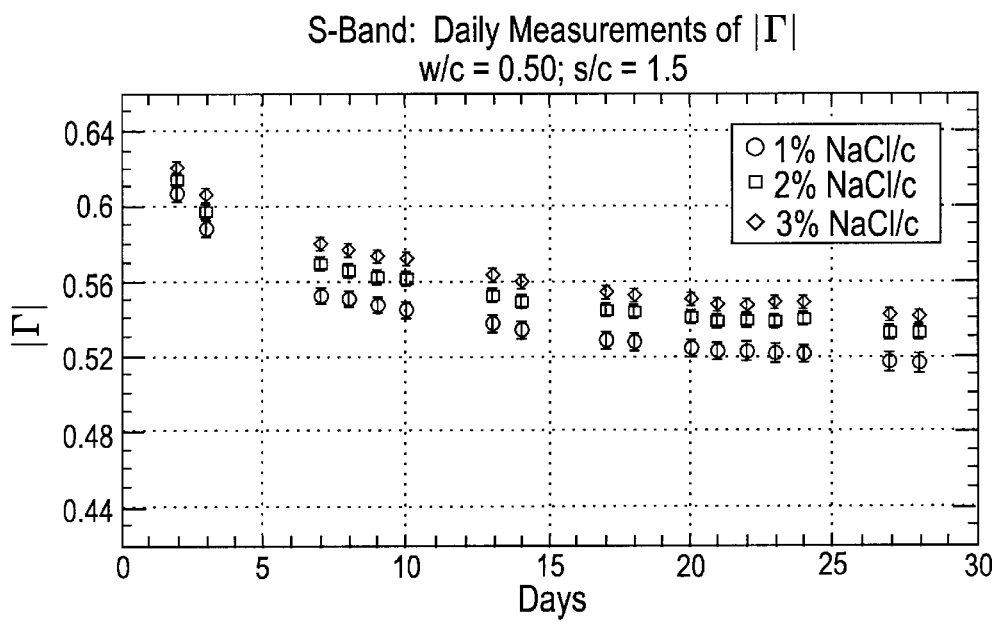
FIG. 3 is a graph illustrating magnitudes of reflection coefficients for cement specimens measured at S-band (3 GHz) having known amounts of sodium chloride.
Figure 4:
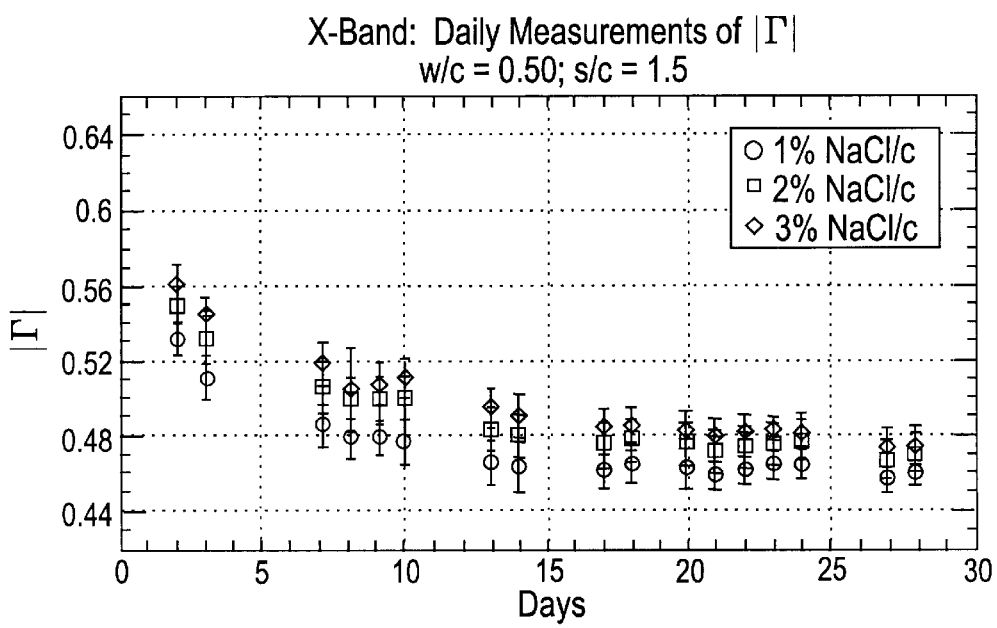
FIG. 4 is a graph illustrating magnitudes of reflection coefficients for cement specimens measured at X-band (10 GHz) having known amounts of sodium chloride.
Figure 5:
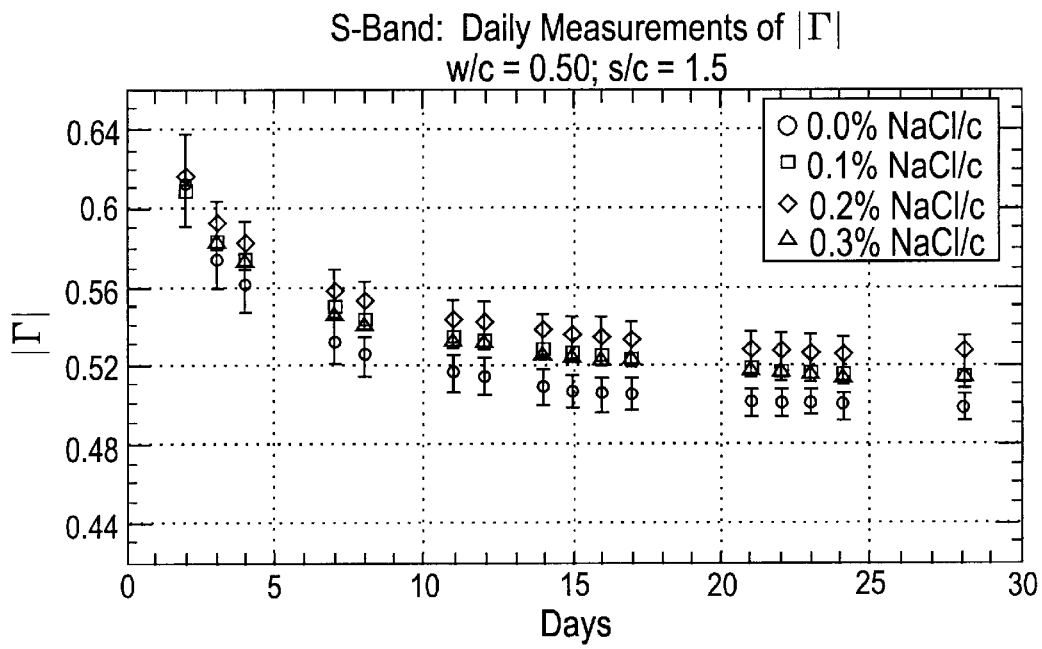
FIG. 5 is a graph illustrating magnitudes of reflection coefficients for cement specimens measured at S-band having less amounts of sodium chloride than FIG. 3.
Figure 6:
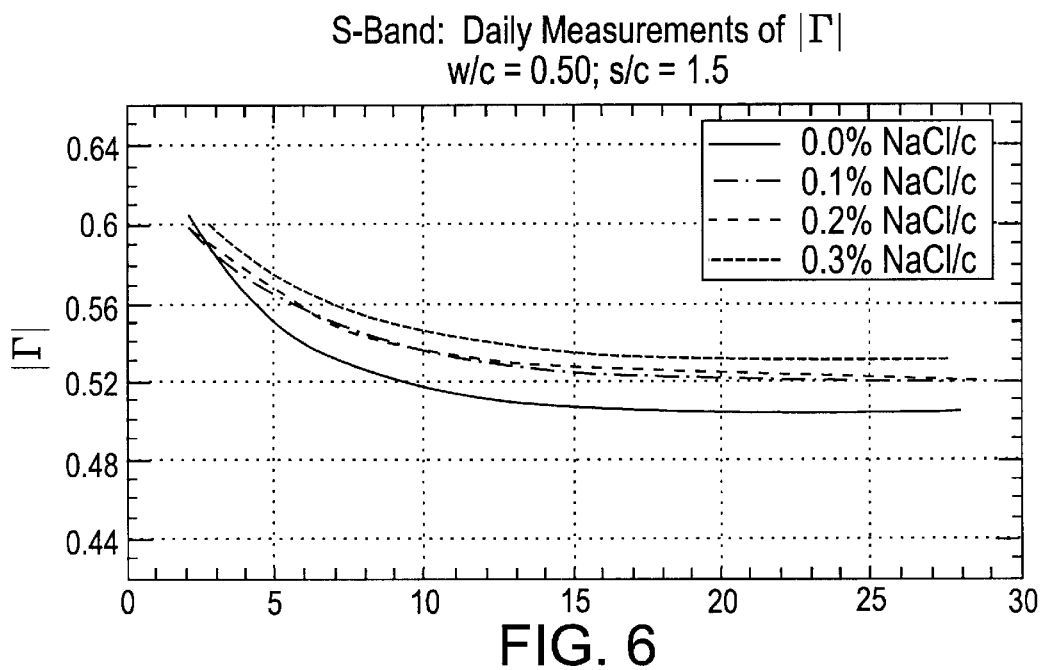
FIG. 6 is a graph illustrating curve fits of magnitudes of reflection coefficients for cement specimens measured at S-band for the amounts of sodium chloride of FIG. 5.
Figure 7:
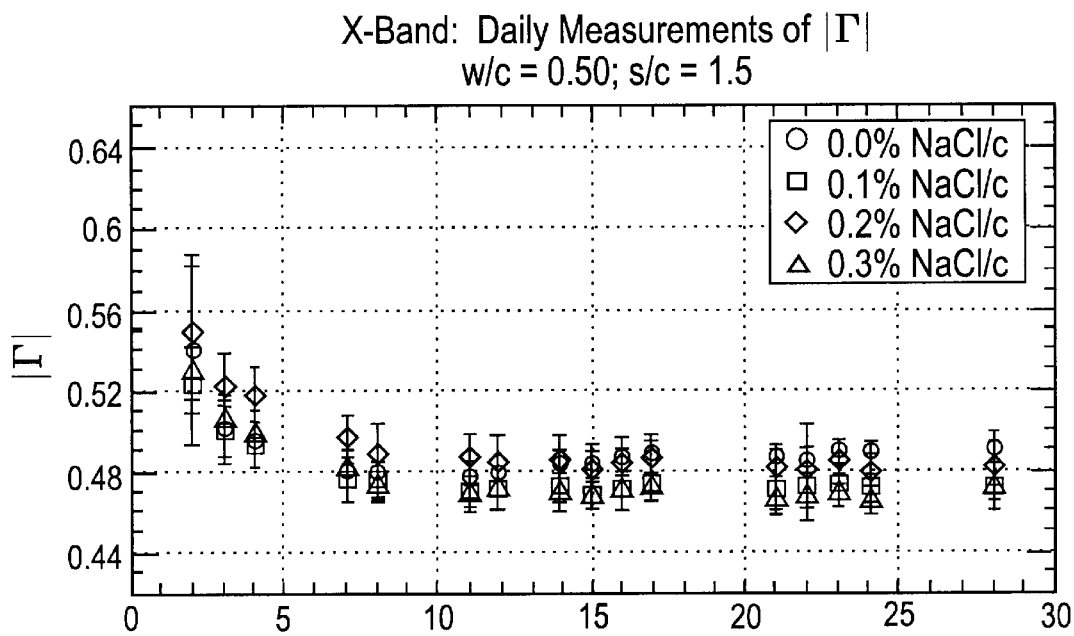
FIG. 7 is a graph illustrating magnitudes of reflections coefficients for cement specimens measured at X-band having less amounts of sodium chloride than FIG. 4.
Figure 8:
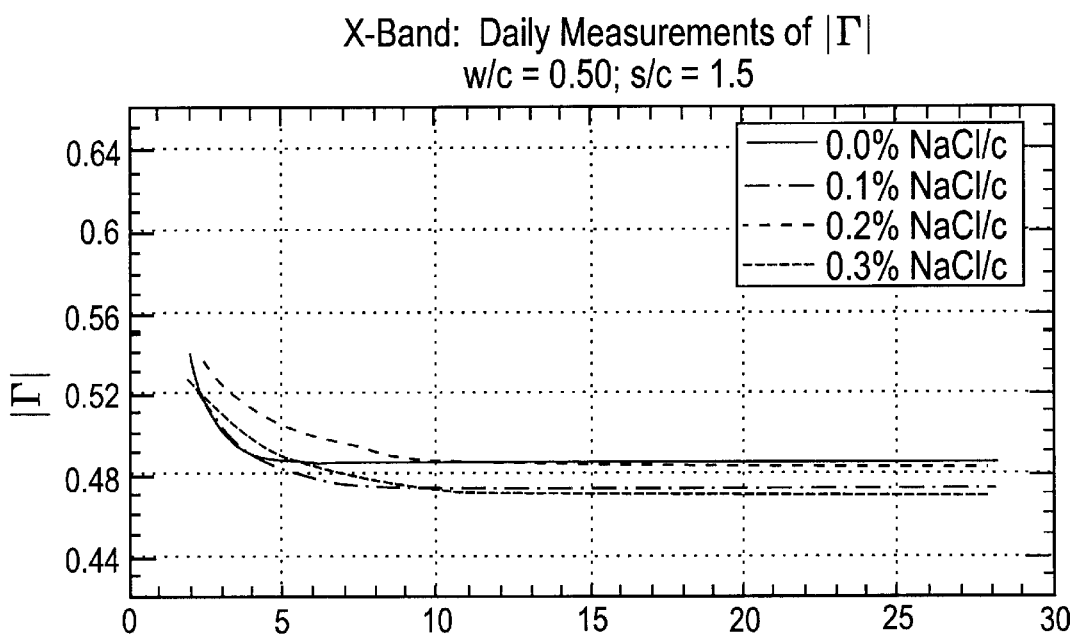
FIG. 8 is a graph illustrating curve fits of magnitudes of reflection coefficients for cement specimens measured at X-band for the amounts of sodium chloride of FIG. 7.
Figure 9:
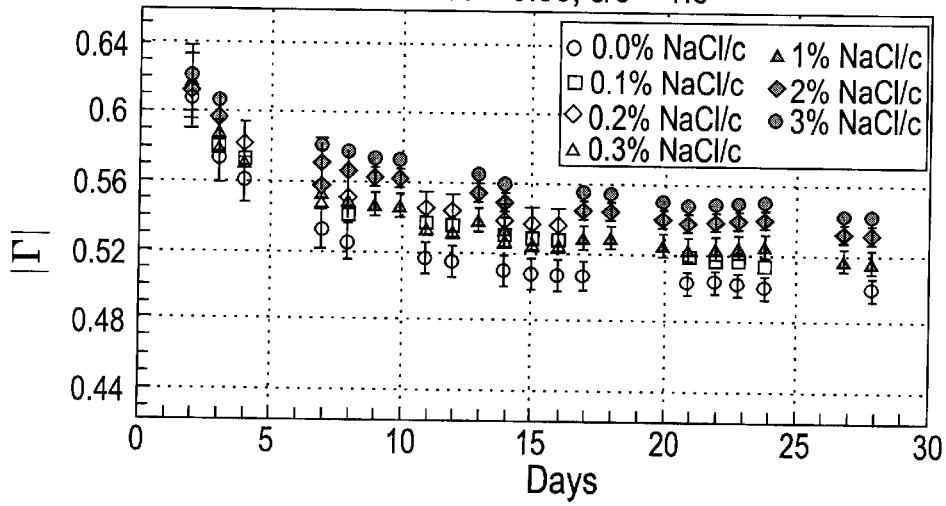
FIG. 9 is a graph illustrating magnitudes of all reflection coefficients for the cement specimens measured at S-band.
Figure 10:
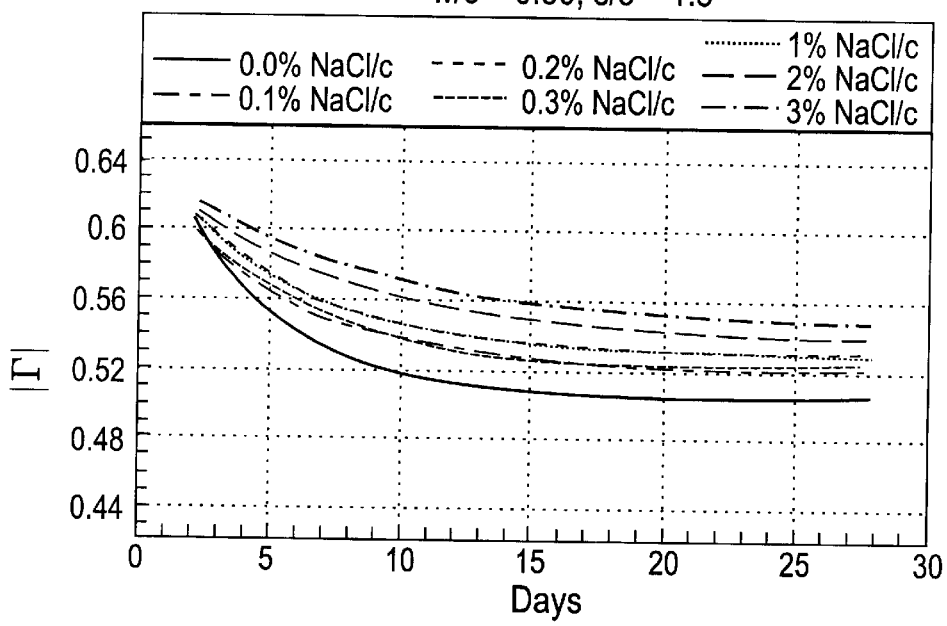
FIG. 10 is a graph illustrating curve fits of magnitudes of all reflection coefficients for the cement specimens of FIG. 9.

FIGS. 7 and 8 show the measurements of $|\Gamma|$ at 10 GHz (X-band) for certain specimens. At the end of the 28 day curing period, the measurements of $\Gamma$ are greater for 0.50 w/c ratios than for 0.60 w/c ratios. This is due to the fact that for any mortar specimen there is a finite amount of cement that the water can bind to. Any free water will simply evaporate. In specimens with 0.50 w/c ratio, there is more cement from which the water can bind to and therefore this specimen will contain more bound water. Microwaves are still sensitive to bound water. Therefore, the measurement of $|\Gamma|$ is expected to be greater for specimens with lower w/c ratio. For the present problem of chloride detection and content determination, we see that the data shown with X-band frequencies is not very conclusive, since the difference in the measurement of $|\Gamma|$ as a function of chloride content is not practically measurable. At 10 GHz there is less distinction between the permittivity for varying NaCl/c. Since the measurement of $|\Gamma|$ is proportional to the dielectric property of the specimen, less difference is expected in the measurement in this frequency range. Ideally, the measurements should be performed at lower frequencies (i.e., S-band). FIGS. 3 and 5 prove the reliability of $|\Gamma|$ as a function of chloride content. At day 28, the distinction between $|\Gamma|$ distinguishable as compared to the 10 GHz plots. Given that these points are distinguishable, data is prepared using the S-band frequencies.

Figure 13:
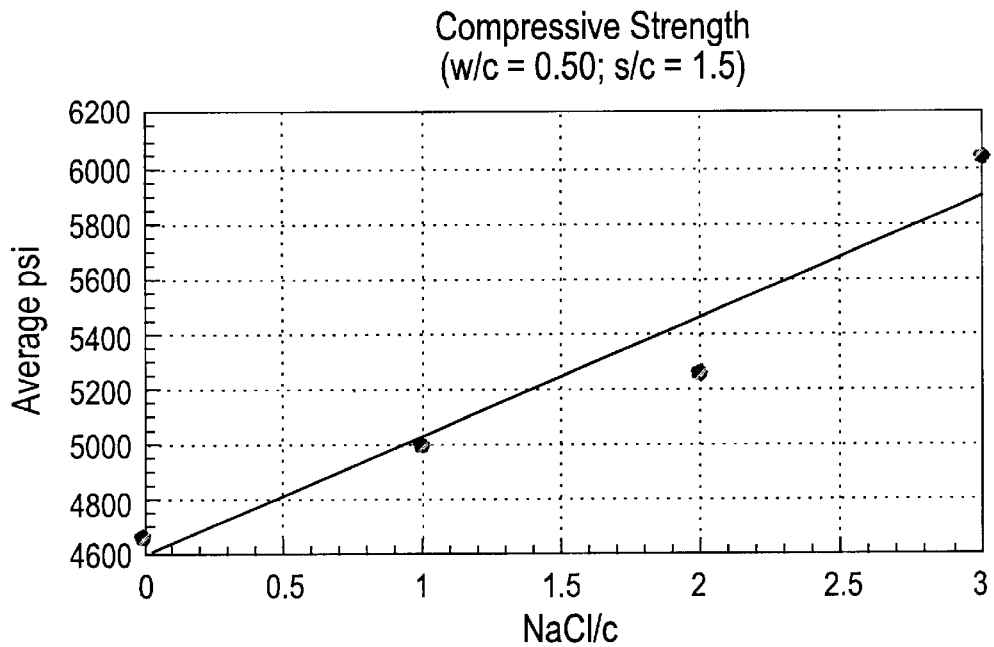
FIG. 13 is a graph of concrete compressive strength vs. amounts of sodium chloride for a w/c ratio of 0.50.
Figure 14:
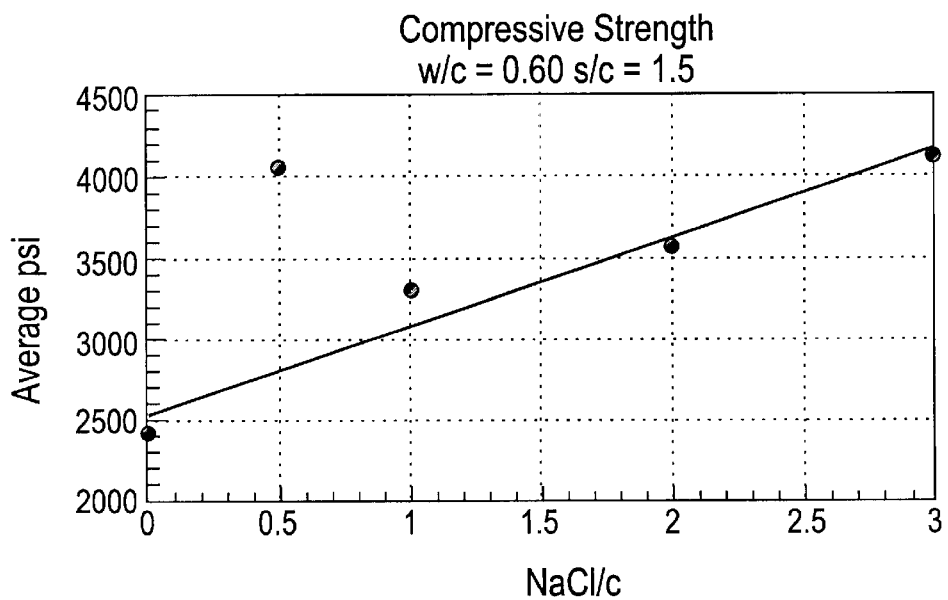
FIG. 14 is a graph of concrete compressive strength vs. amounts of sodium chloride for a w/c ratio of 0.60.

FIGS. 13 and 14 show the compressive strength of the cylinders after the 28-day curing period. Here the compressive strength of specimens with 0.50 w/c ratio is expected to be higher than that with 0.60 w/c ratio. This behavior would conform to Abrahm's Law. These figures show that w/c= 0.60 has less strength than the w/c =0.50. Additionally, per given w/c ratio, the compressive strength increases linearly as a function of NaCl/c ratio. Therefore one could be lead to believe that from a compressive strength standpoint, the addition of chloride in cement based materials is beneficial. However, the downside to this stream of thought is that the protective film mentioned earlier has a greater risk of breaking down and deteriorating the steel members. This would compromise the structural integrity of the structure (reduce lateral load resistance) and possibly degrade its compressive strength.

Figure 15:
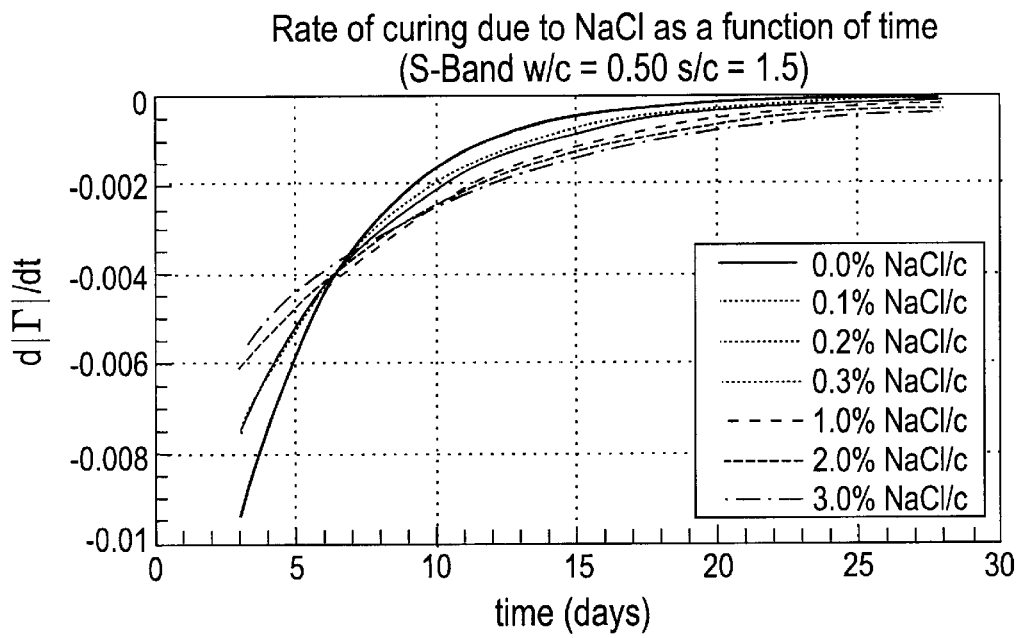
FIG. 15 illustrates concrete strength curves due to the presence of sodium chloride with a w/c ratio of 0.50.
Figure 16:
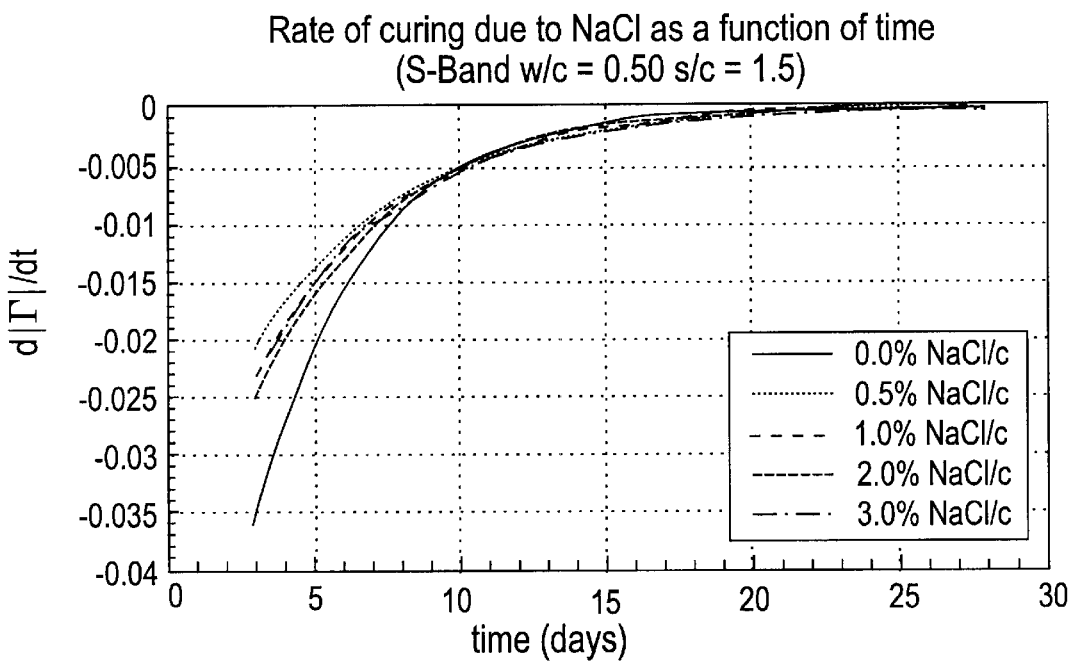
FIG. 16 illustrates concrete strength curves due to the presence of sodium chloride with a w/c ratio of 0.60.

In FIGS. 15 and 16, the influence of chloride content on curing rate ($\partial |\Gamma|/\partial t$) is addressed. The addition of chloride in cement based materials will accelerate its initial setting time (i.e., hardening) but not change its final curing time. Therefore a greater percent of the initial curing process would occur in the first day of curing for the chloride contaminated specimens. This would translate into less change in $|\Gamma|$ as a function of days for the remainder of the 28-day curing period, and a smaller reading of $\partial |\Gamma|/\partial t$. From FIGS. 15 and 16, we see that the specimen with 0.0% NaCl/c (non-contaminated specimen) takes more time to set, and therefore the measurement of a $\partial |\Gamma|/\partial t$ is greater in the first days of curing. However, the total curing time is not reduced by the present chloride, since all mixtures converge to their final value of $|\Gamma|$ after approximately 16–17 days (i.e., 0).

Figure 17:
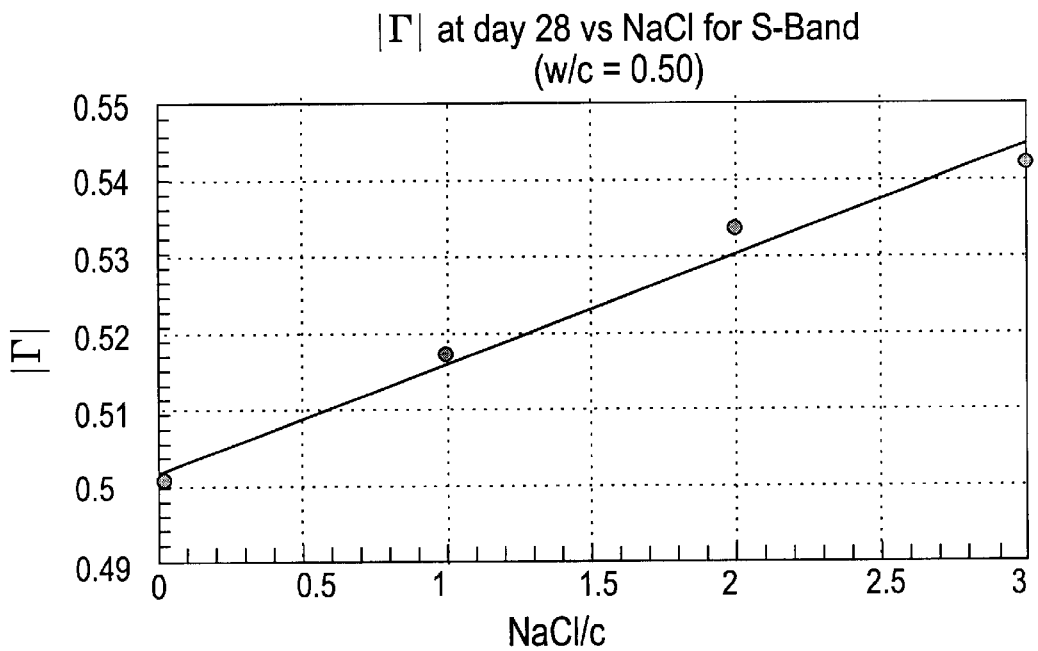
FIG. 17 is a graph of magnitudes of reflection coefficients as a function of the amount of sodium chloride after the cured specimen has been in a sodium chloride bath for 28 days and where the w/c ratio is 0.50.
Figure 18:
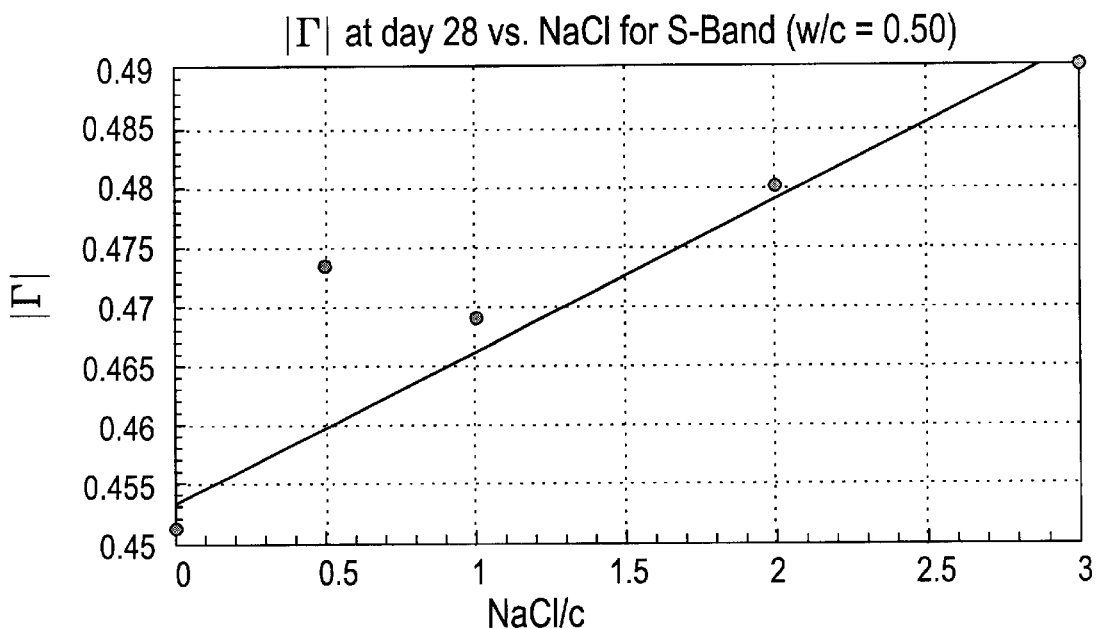
FIG. 18 is a graph illustrating the magnitudes of reflection coefficients as a function of the amount of sodium chloride at day 28 when the w/c ratio is 0.60.
Figure 19:
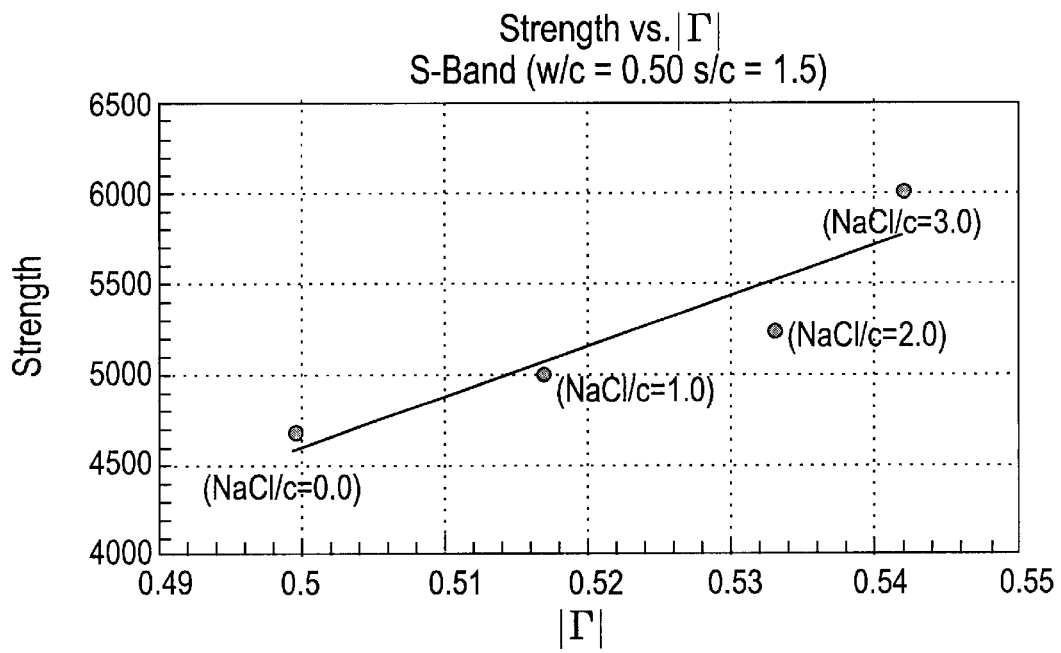
FIG. 19 is a graph illustrating concrete compressive strength as a function of magnitudes of reflection coefficients for certain amounts of sodium chloride at day 28 when the w/c ratio is 0.50.
Figure 20:
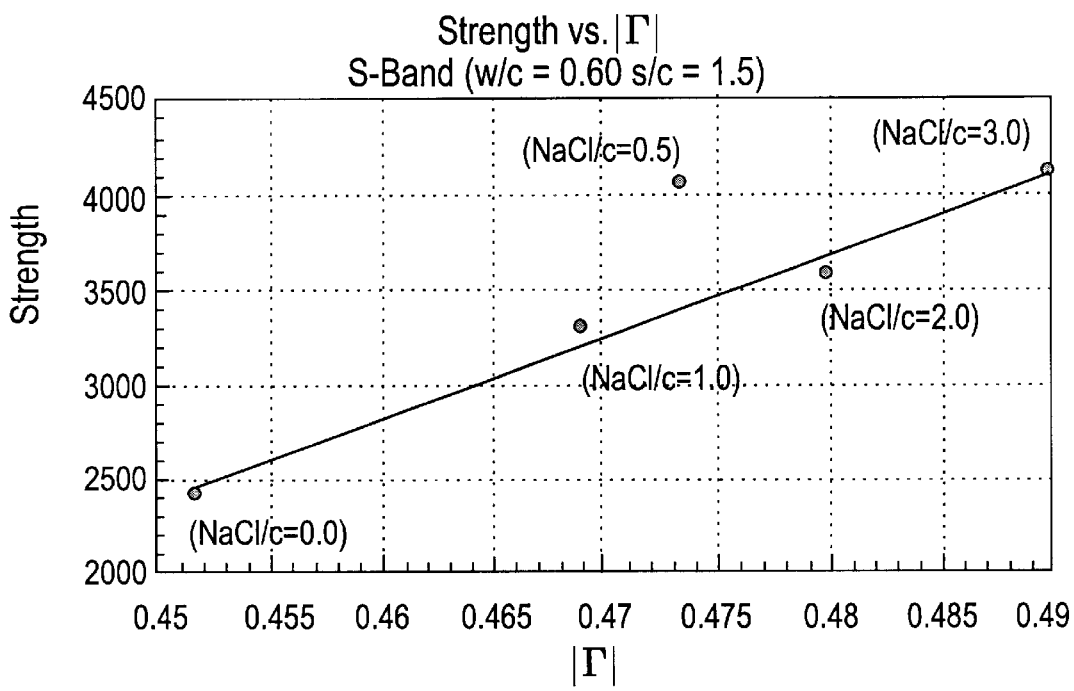
FIG. 20 is a graph illustrating concrete compression strength as a function of the magnitudes of reflection coefficients for certain amounts of sodium chloride at day 28 when the w/c ratio is 0.60.
Figure 21:
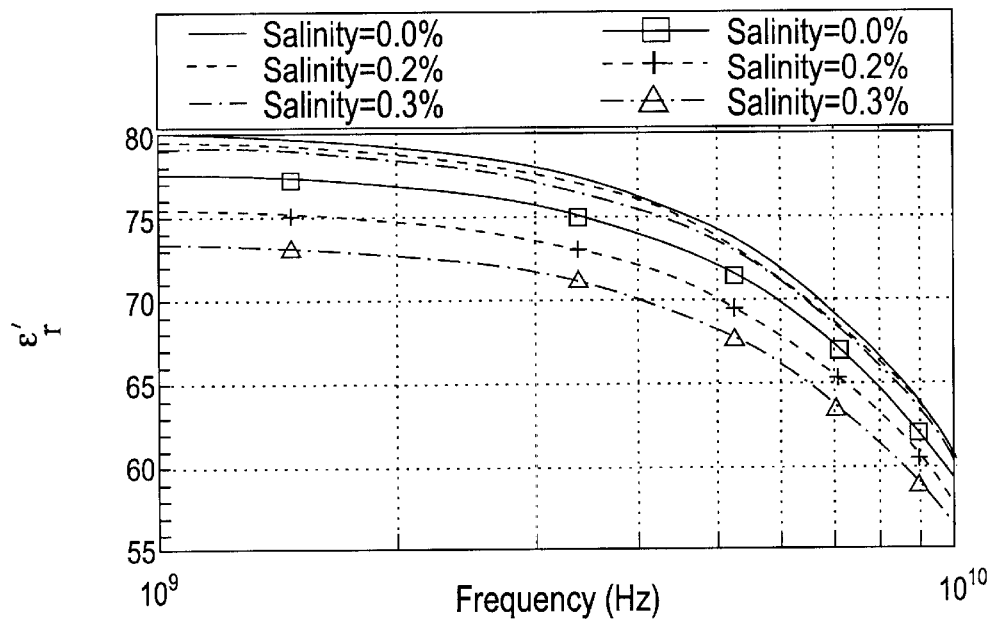
FIG. 21 is a graph illustrating the relative permittivity of water as a function of frequency for different amounts of salinity.
Figure 22:
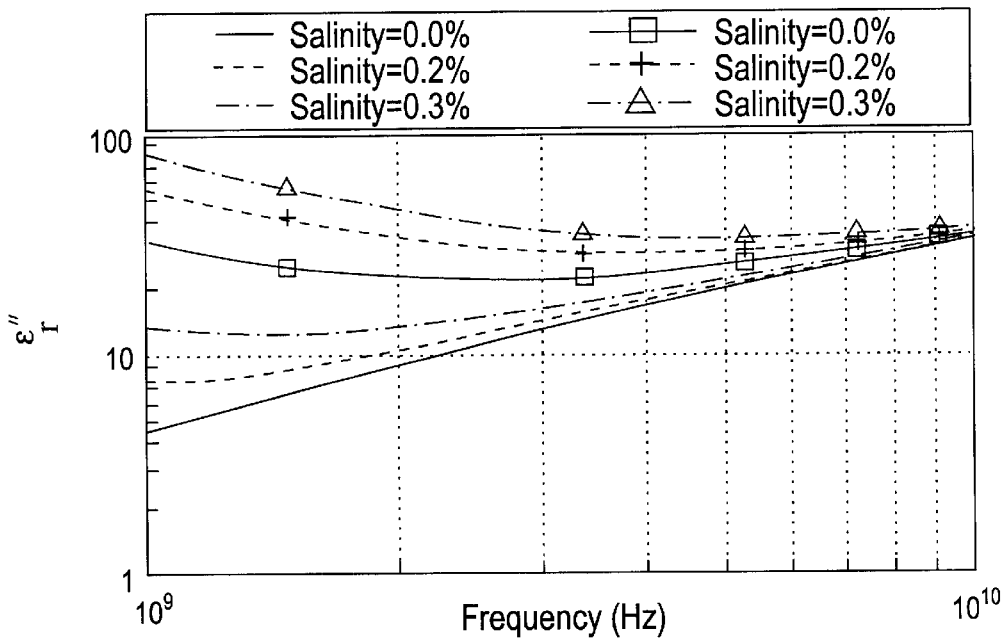
FIG. 22 is a graph illustrating the loss factor of water as a function of frequency for different amounts of salinity.

Lastly, since the effect of NaCl/c on the measurement of $|\Gamma|$ and compressive strength has been discussed, it would be interesting to determine if one could determine a relationship of $|\Gamma|$ vs. compressive strength. In FIGS. 17 and 18, there is a linear relationship between NaCl/c and measurements of $|\Gamma|$. In FIGS. 19 and 20, it is shown that compressive strength increases linearly with respect to NaCl/c ratio. Therefore the relationship between $|\Gamma|$ and compressive strength should also be linear. This behavior is readily observed in FIGS. 19 and 20. Therefore the nondestructive determination of compressive strength of mortar as a function NaCL/c ratio could be possible by using a linear interpolation scheme with respect to an uncontaminated specimen. FIG. 21 indicates that the relative permittivity of water for different salinities decreases as a function of frequency. FIG. 22 illustrates that the loss factor of water increases with greater salinity and the differences therebetween can be more readily determined at relatively lower frequencies.

Figure 23:
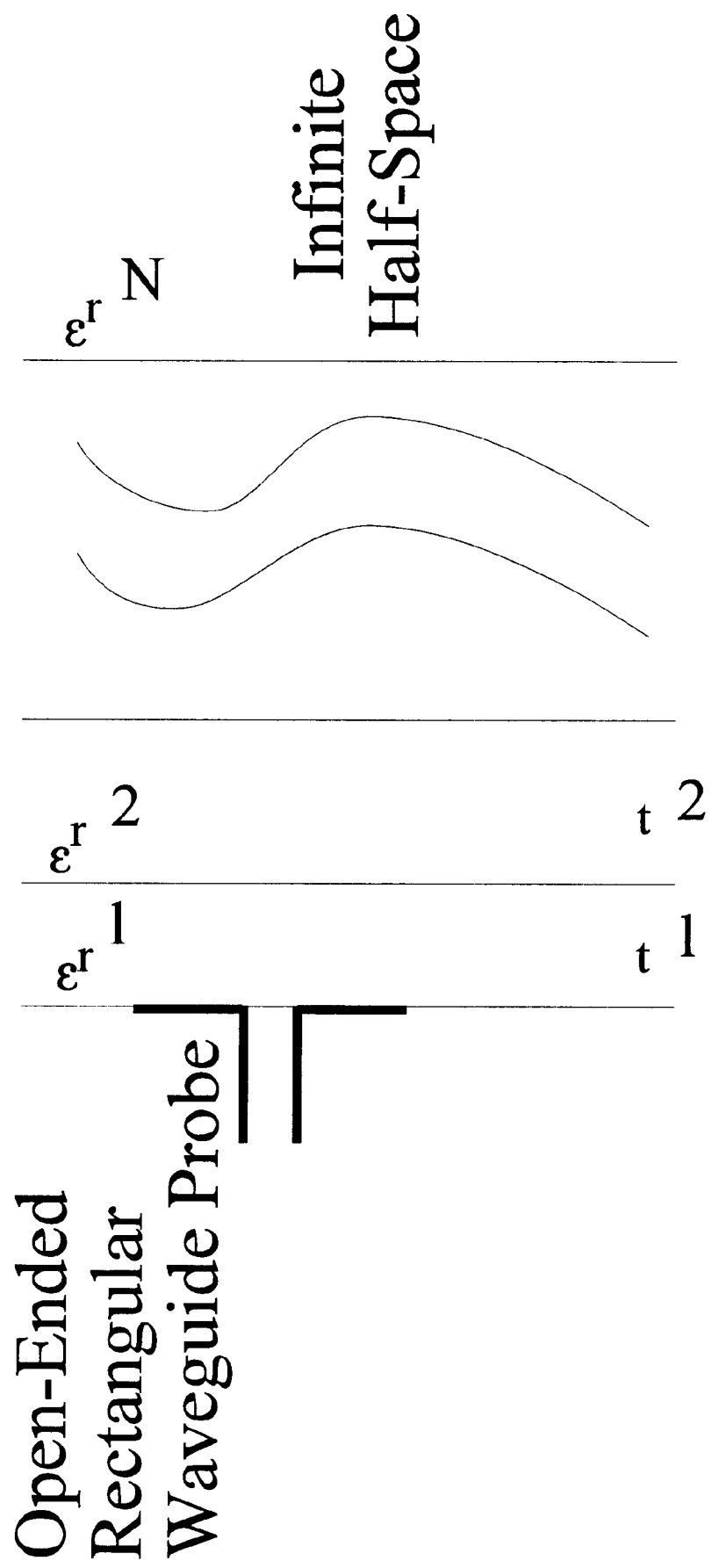
FIG. 23 diagrammatically illustrates a multi-layered dielectric composite structure under inspection using a coupler subsystem (e.g., an open-ended rectangular wave guide)

With reference to FIG. 23, an electromagnetic theoretical model for calculating the reflection properties of a multi-layered dielectric composite structure inspected by an open-ended rectangular waveguide has been developed. The input parameters to this model include the frequency of operation, the number of layers, the thickness of each layer (t) and the dielectric properties ($\epsilon_r$) of each layer.

Consider each specimen to be modeled as a multi-layered material after successive exposure to the chloride solution. As mentioned earlier, it is intended to use relatively low microwave frequencies for all specimens including concrete. Consequently, all specimens can be considered to be homogeneous at these frequencies, and the influence of discrete aggregates in concrete will be at best minimal and can be neglected. Hence, the homogeneous layered model of a concrete specimen is valid for this modeling effort. For each specimen, its dielectric properties will be calculated from its measured reflection coefficient before it is exposed to chloride and after exposure to successive accelerated chloride contamination. This information is then used as a close estimate of the dielectric properties of each layer of the discretely modeled specimen. From the actual measurements of some of the drilled cores, we will obtain information about the manner by which the chloride has penetrated into each specimen. From this information a certain trend for chloride penetration into the specimen can be formed; namely, a linear or exponential chloride penetration trend. Additionally, the depth to which chloride may have penetrated will also be known. Subsequently, using these pieces of information we can discretize the depth of penetration to estimate the number of layers for the model and their respective dielectric properties. Once the reflection coefficient of a specimen is calculated using this model, it will be compared to the measured reflection coefficient. The dielectric property trend (indicator of the trend of chloride penetration) and the number of layers will then be iteratively modified to get a closer agreement between the measured and the calculated reflection coefficients. The results of this model can then be used as a predictor of chloride content and the extent (depth) of its penetration for unknown concrete specimens in practical environments. This is to say that once the reflection coefficient of an unknown concrete specimen is measured the chloride level and its depth of penetration may be determined using the results of this model.

Figure 24:
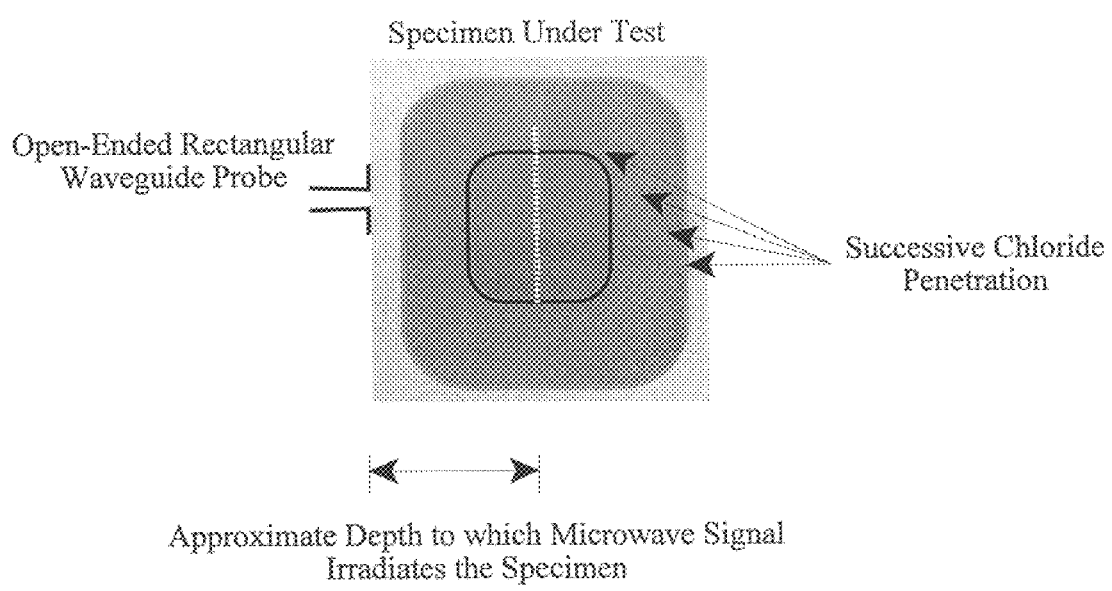
FIG. 24 diagrammatically illustrates a concrete specimen under test using the coupler subsystem related to penetration of the predetermined material, such as chloride, into the specimen.
Figure 25:
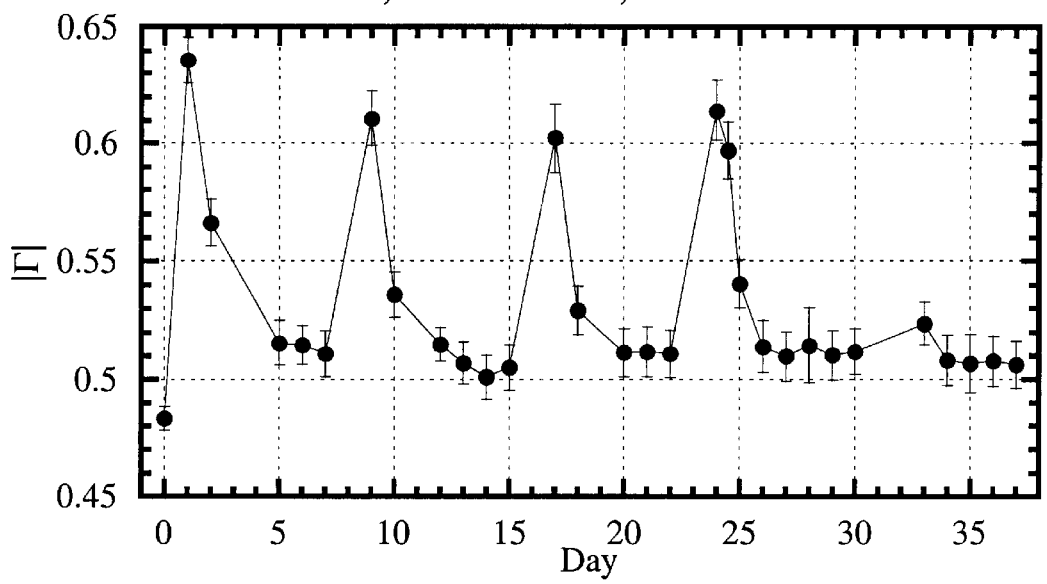
FIG. 25 is a graph illustrating magnitudes of reflection coefficients measured over time when calcium chloride is present.
Figure 26:
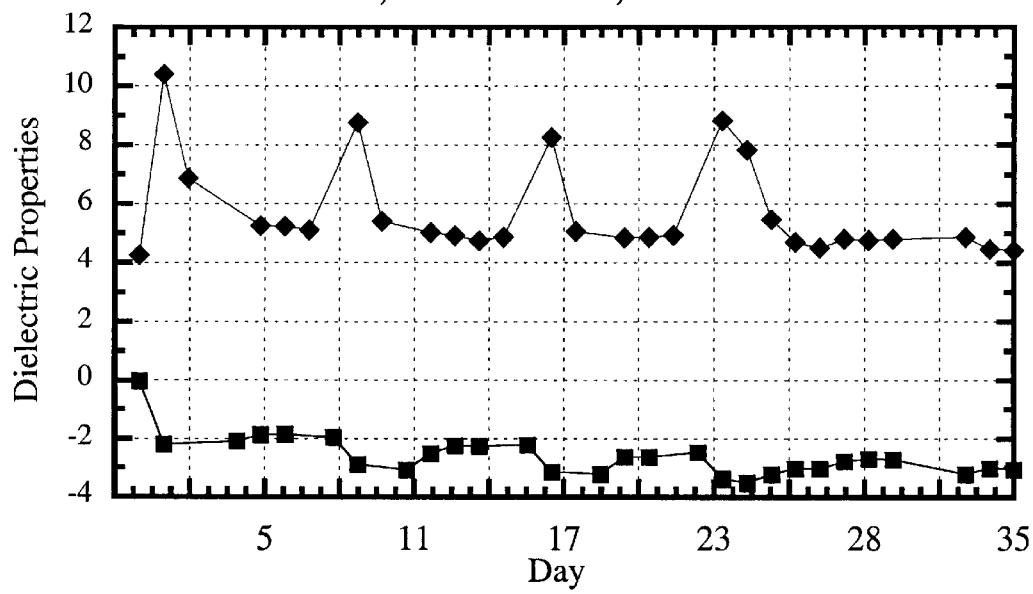
FIG. 26 is a graph illustrating dielectric properties measured over time when calcium chloride is present.
Figure 27:
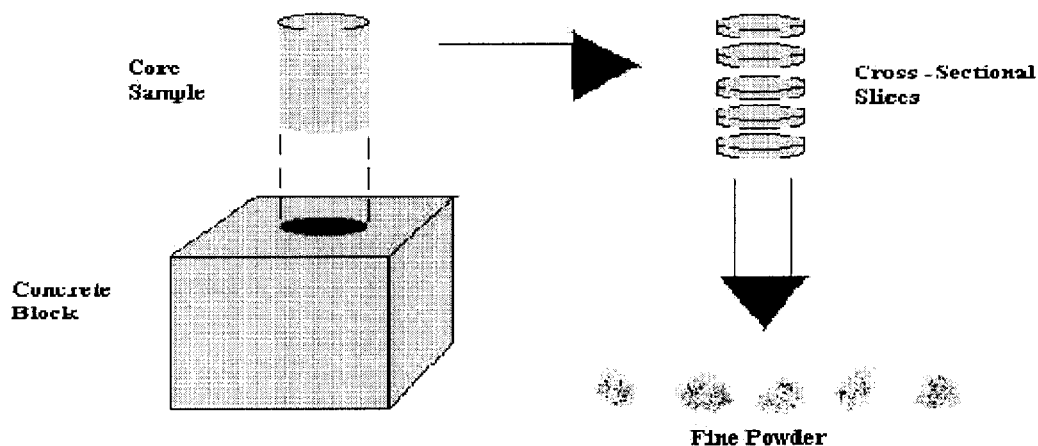
FIG. 27 diagrammatically illustrates a number of steps related to analyzing a cored concrete section.
Figure 28:
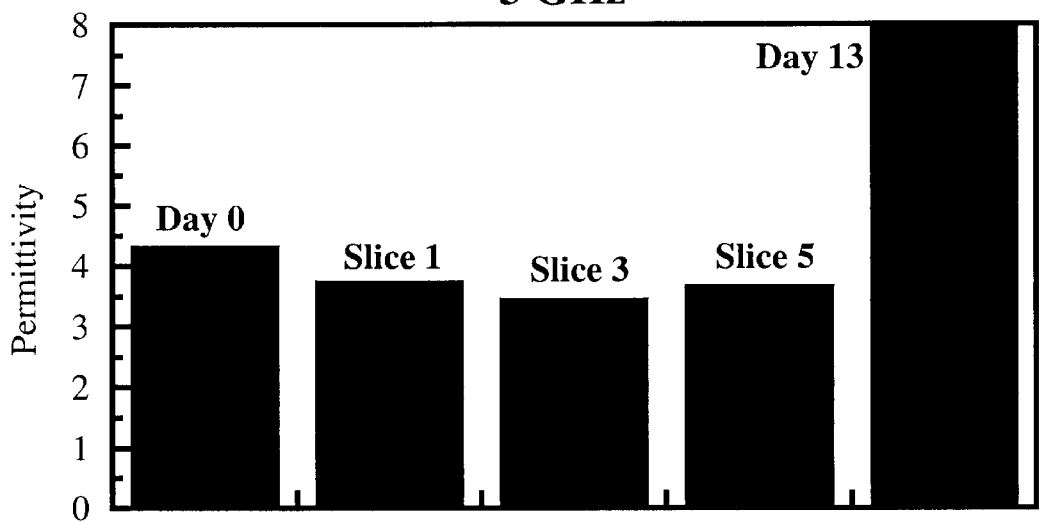
FIG. 28 is a bar graph illustrating permittivity for a number of cored slices for a concrete specimen.
Figure 29:
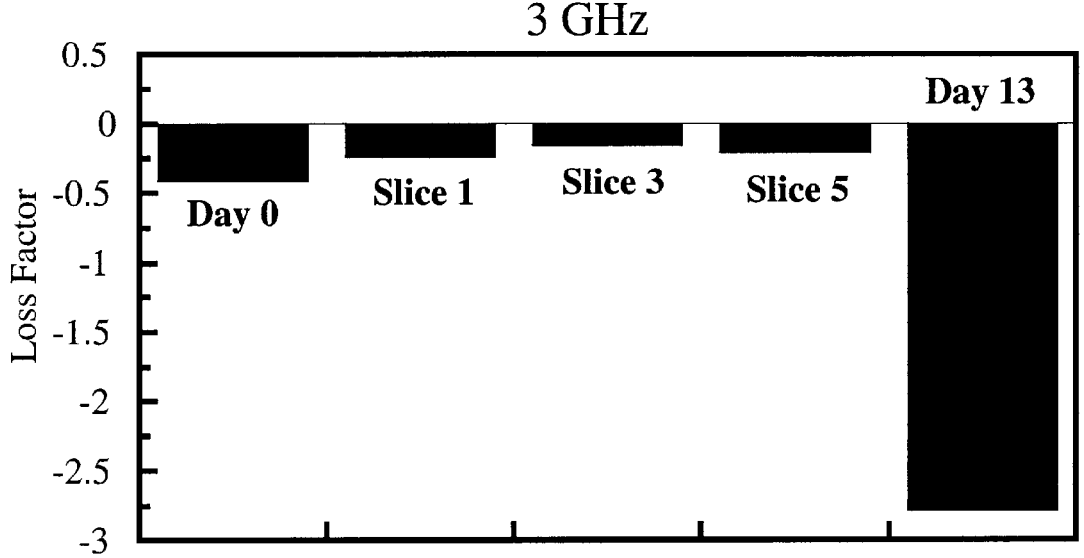
FIG. 29 is a bar graph illustrating loss factor for number of cored slices for a concrete specimen.
Figure 30:
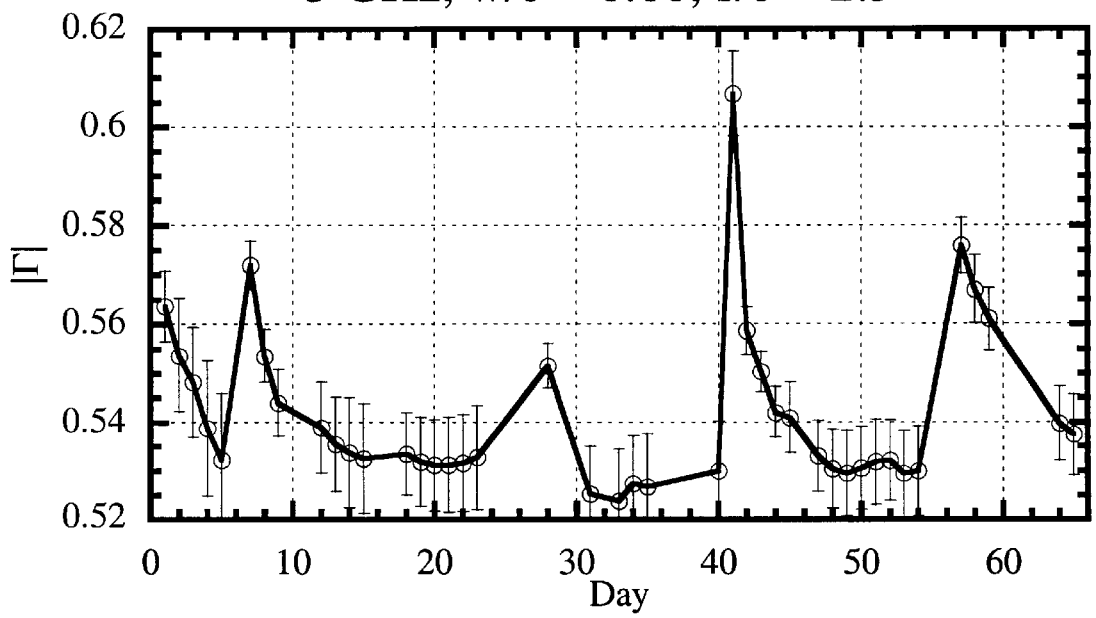
FIG. 30 is a graph illustrating magnitudes of reflection coefficients measured over a longer period of time for concrete specimens when sodium chloride is present.
Figure 31:
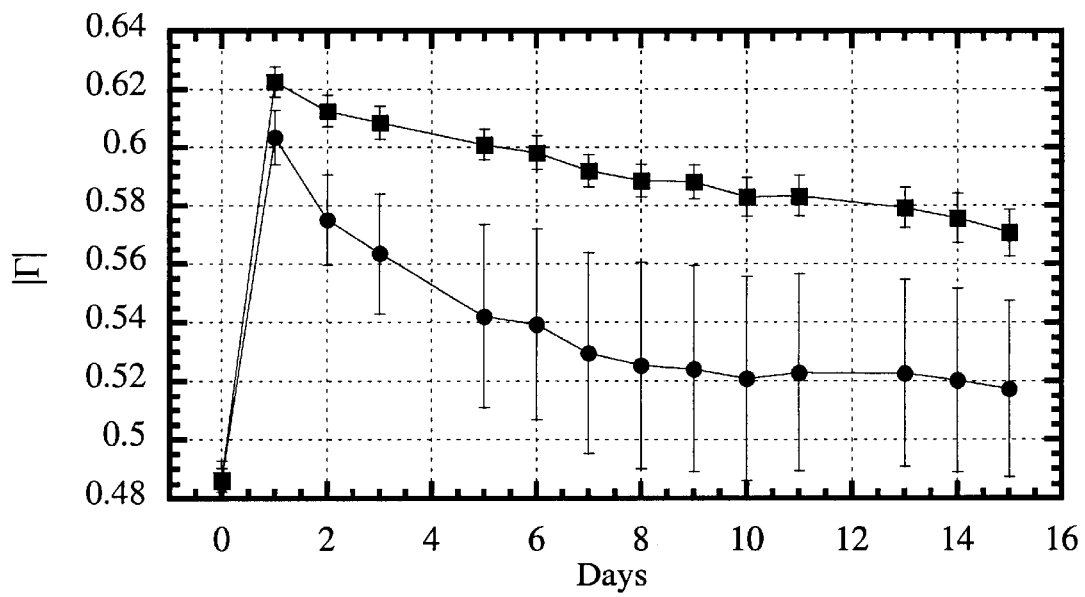
FIG. 31 is a graph illustrating magnitudes of reflection coefficients measured over time for tap water and salt water.
Figure 32:
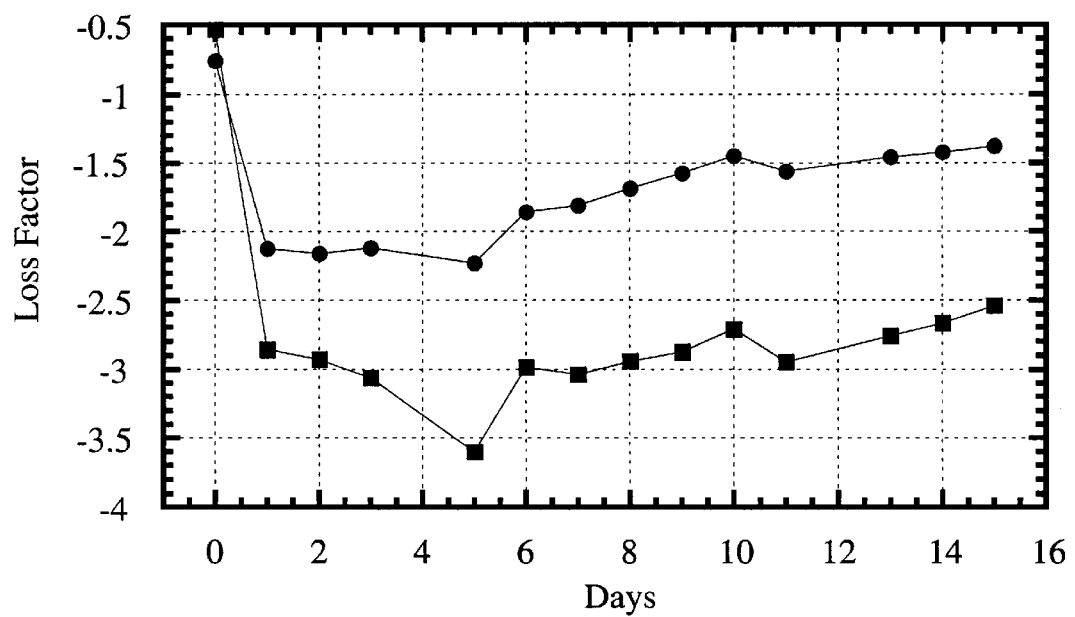
FIG. 32 is a graph of loss factor measured over time for tap water and salt water.
Figure 33:
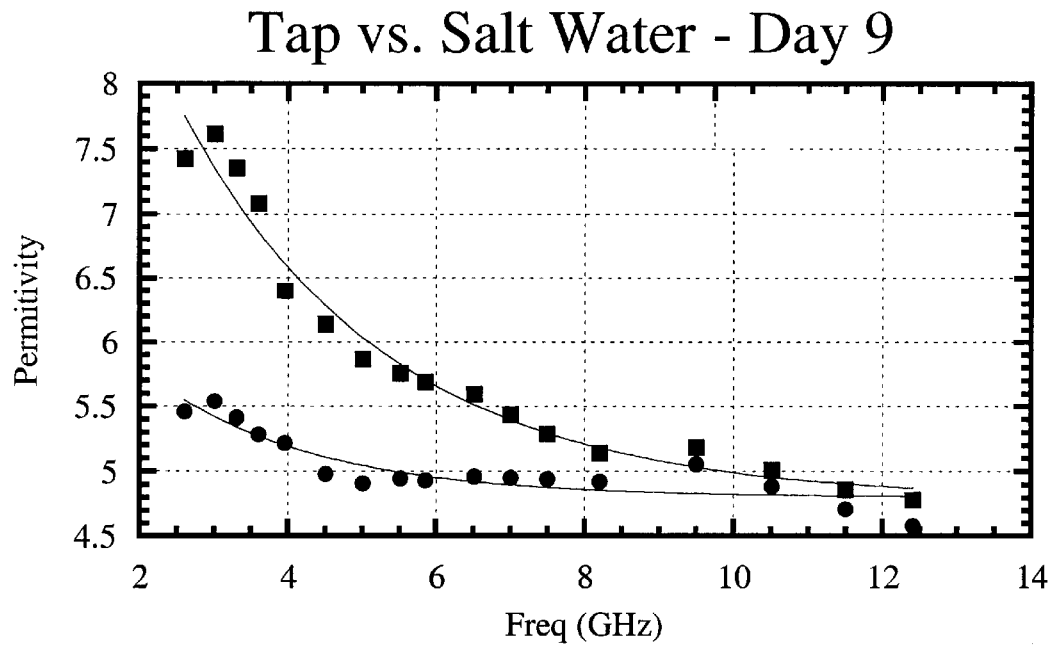
FIG. 33 is a graph illustrating permittivity as a function of frequency for tap water and salt water at day 9.
Figure 34:
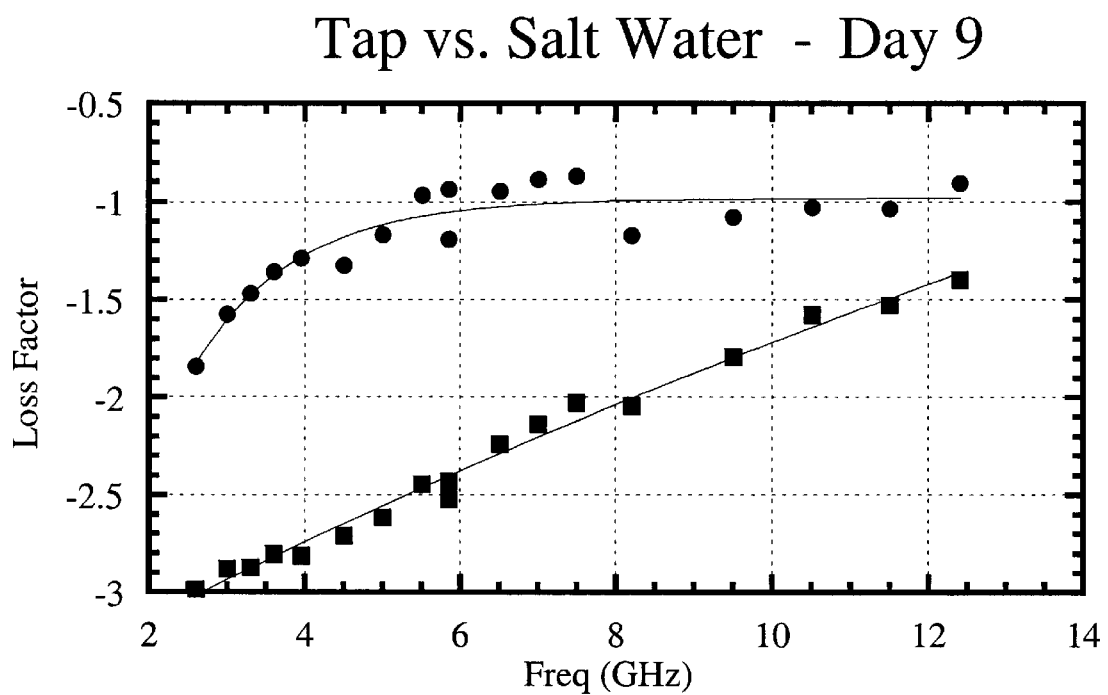
FIG. 34 is a graph illustrating loss factor as a function of frequency for tap water and salt water at day 9.

With reference to FIG. 24, the depth to which a microwave signal penetrates inside a dielectric material, such as the specimens of interest in this proposal, is a function of the dielectric properties of the material, the frequency of operation and the incident power level. In addition, this parameter is also influenced by the sensitivity of the apparatus (including a HP8510 network analyzer in this case) since a more sensitive detector allows reflected signals from deeper portions of a material to be detected. For the frequencies of interest and the concrete based materials for investigation, using the HP8510 network analyzer, the depth from which the reflected signal may be detected is several centimeters (7–10 cm). The dashed line in FIG. 24 qualitatively shows the approximate relative depth from which the microwave signals in previous investigations have been detected.

This depth of microwave signal penetration also closely follows the depth at which reinforcing bars are located in practical reinforced concrete. If deeper interrogation of a concrete specimen is required, then one may increase the incident microwave power level.

Microwave NDT determination of content and curing effect of chloride in cement based materials was successfully demonstrated. The work done in this area can be effective in using the near-field techniques discussed above. The research done to this point has strong implications in that chloride detection is feasible. The data shows that by using S-band frequencies and analyzing the magnitude of reflection coefficient, detection between uncontaminated and contaminated specimens can be accomplished. The information provided can relate the linear increase in magnitude of reflection coefficient to the increase in compressive strength. This connects the electrical properties to the mechanical properties. Although, adding chloride to the cement materials appears to increase the compressive strength, there is also greater risk of deteriorating the steel members. This would compromise the structural integrity of the structure and possibly degrade its compressive strength.

More information is next provided including FIGS. 25–34 related to penetration of salt or chloride material in cement or mortar specimens. From this, chloride model information can be ascertained related to establishing a model, such as in the form of a graph, an equation, and/or data in a look-up table, related to correlating dielectric property information (e.g., related to the magnitude of the reflection coefficient) and chloride content information in the cement specimen. Among the steps conducted and relevant background information are the following:

Mortar specimens are prepared with varying w/c and s/c. The cured specimens are placed in a salt bath for a known time and then removed (FIG. 2). The reflection properties of these specimens are measured using open-ended rectangular waveguides at microwave frequencies (FIG. 1).

The specimens are cored and their dielectric properties are measured as a function of depth into these specimens. A multi-layer electromagnetic code is used to predict the amount and depth of chloride penetration. A determination is made whether such models can be eventually used for predicting chloride content and depth to which it may have penetrated.

Chloride ions can be introduced in cement-based structures in different ways: (a) during its manufacture: (i) mixing water and (ii) in the sand and aggregate; (b) after the construction of a structure: (i) de-icing salts and (ii) exposure to salt air.

Various amounts of table salt were added to the mixing water of various cement paste and mortar specimens. The specimens were moist-cured for one day and then cured at room temperature and humidity for the remainder of the prescribed 28-day period. Their reflection properties were measured daily at S- and X-band.

The magnitude of reflection coefficient, $|\Gamma|$, showed to be a useful parameter for detecting and evaluating the presence of salt. $|\Gamma|$, at 3 GHz (S-band), was correlated to the salt content and the compressive strength of these specimens. This correlation was shown to be systematic as a function of w/c in mortar.

A mortar specimen can be placed into salt water for a certain amount of time (originally under pressure). Calcium chloride was used as well sodium chloride. The specimen was dried in the ambient environment for approximately 24 hours. The reflection coefficient of the specimen was measured daily until no change was sensed.

This process was repeated for a few cycles. The specimen was cored, cut and ground. Their dielectric properties were measured. Core samples were analyzed using electron microscopy and X-ray fluorescence. Such data was attempted to be correlated with the chloride ingress.

A monopole antenna probe may be useful in connection with making measurements to determine information related to materials found in fresh cement paste and concrete, such as the water/cement (w/c) ratio and/or chloride content. A monopole probe is similar in shape and size to a pin with a needle-like probe extending from its end, which can be inserted, for example, into fresh cement paste. The microwave properties of a monopole probe are controlled by it length, frequency of operation, the coaxial line geometry used to excite it and the dielectric properties of the medium surrounding it (e.g., fresh Portland cement-based material). As this medium changes from free space to fresh cement paste, as this probe is inserted into a fresh batch of concrete, so do the measured microwave reflection properties of the monopole. This information can be obtained in real-time and it is anticipated that such can be correlated to chloride content and/or the w/c ratio. When the probe is inserted to a fresh batch of concrete, the influence of aggregates can be reduced or eliminated by the choice of the operating frequency, monopole size and operating microwave power.

A typical monopole probe is an extension of an inner conductor of a coaxial transmission line whose outer conductor is commonly terminated in an infinite ground plane (in theory). In practice and depending on the dielectric properties of the medium under inspection, the extent of this ground plane may be relatively small or it may be altogether eliminated. Based on the dielectric properties of the medium, such as fresh cement paste, the probe design can be optimized for determining optimal dimensions thereof, as a function of frequency. The optimal probe dimensions (e.g., length and diameter) are those which give higher sensitivity to the measurement being made, such as related to chloride content and/or w/c ratio.

The foregoing discussion of the invention has been presented for purposes of illustration and description. Further, the description is not intended to limit the invention to the form disclosed herein. Consequently, variations and modifications commensurate with the above teachings, within the skill and knowledge of the relevant art, are within the scope of the present invention. The embodiments described hereinabove are further intended to explain the best modes presently known of practicing the invention and to enable others skilled in the art to utilize the invention in such, or other embodiments, and with the various modifications required by their particular application or uses of the invention. It is intended that the appended claims be construed to include alternative embodiments to the extent permitted by the prior art.

What is claimed is:

1. An apparatus for making determinations related to a predetermined material in a cement sample, comprising:

a signal generating subsystem for outputting microwave signals;

a coupler subsystem for transmitting microwave signals received from said signal generating subsystem and for receiving return signals from the cement sample; and an analyzing subsystem in communication with said coupler subsystem that determines information related to the presence of predetermined material in the cement sample, said analyzing subsystem including at least one memory that stores model information related to correlating dielectric property information and content of predetermined material in the cement sample, said model information being based on a number of cement specimens including first and second cement specimens, the first and second cement specimens after being cured having been subjected to at least a first amount of predetermined material for first and second time periods, respectively, said at least first amount of predetermined material being one that is not normally included when the first and second cement specimens are formed, said model information also being based on transmitted and received microwave signals relating to the first and second specimens after being cured and after being subjected to said at least first amount of predetermined material and in which said received microwave signals from the first and second specimens after being cured are indicative of absorption of said transmitted microwave signals by the first and second cement specimens due to them having been subjected to said at least first amount of predetermined material, wherein said at least first amount of predetermined material to which the first cement specimen was subjected is greater than predetermined material, if any, in the first cement specimen before being subjected to said at least first amount of predetermined material.

2. An apparatus, as claimed in claim 1, wherein:

said model information includes chloride model information.

3. An apparatus, as claimed in claim 1, wherein:

the first cement specimen after being cured has substantially no predetermined material before being subjected to at least said first amount of predetermined material.

4. An apparatus, as claimed in claim 1, wherein:

the first cement specimen after being cured was subjected to an amount of said predetermined material that is greater than said first amount to which the second cement specimen after being cured was subjected.

5. An apparatus, as claimed in claim 1, wherein:

each of the first and second cement specimens was subjected to at least one predetermined pressure different from atmospheric pressure after being cured.

* * * * *